US008076104B2

(12) United States Patent  (10) Patent No.: US 8,076,104 B2
Rogan  (45) Date of Patent: Dec. 13, 2011

(54) RAPID AND COMPREHENSIVE IDENTIFICATION OF PROKARYOTIC ORGANISMS

(76) Inventor: Peter K. Rogan, London (CA)

( * ) Notice: Subject to any disclaimer, the term of this patent is extended or adjusted under 35 U.S.C. 154(b) by 241 days.

(21) Appl. No.: 12/011,425

(22) Filed: Jan. 25, 2008

(65) Prior Publication Data

US 2008/0261222 A1  Oct. 23, 2008

Related U.S. Application Data

(60) Provisional application No. 60/886,595, filed on Jan. 25, 2007.

(51) Int. Cl.
*C12P 19/34* (2006.01)
(52) U.S. Cl. .................................................. 435/91.2
(58) Field of Classification Search ................ 435/91, 435/2
See application file for complete search history.

(56) References Cited

U.S. PATENT DOCUMENTS

| | | | |
|---|---|---|---|
| 5,426,027 A | 6/1995 | Lott et al. | |
| 5,547,835 A | 8/1996 | Koster | |
| 5,622,824 A | 4/1997 | Koster | |
| 5,691,141 A | 11/1997 | Koster | |
| 5,849,492 A * | 12/1998 | Rogan | 435/6 |
| 5,851,765 A | 12/1998 | Koster | |
| 5,872,003 A | 2/1999 | Koster | |
| 6,074,823 A | 6/2000 | Koster | |
| 6,140,053 A | 10/2000 | Koster | |
| 6,194,144 B1 | 2/2001 | Koster | |
| 6,225,450 B1 | 5/2001 | Koster | |
| 6,238,871 B1 | 5/2001 | Koster | |
| 6,268,131 B1 | 7/2001 | Kang et al. | |
| 7,108,974 B2 | 9/2006 | Ecker et al. | |
| 7,217,510 B2 | 5/2007 | Ecker et al. | |
| 7,226,739 B2 | 6/2007 | Ecker et al. | |
| 7,255,992 B2 | 8/2007 | Ecker et al. | |
| 2004/0161770 A1 | 8/2004 | Ecker et al. | |
| 2004/0209260 A1 | 10/2004 | Ecker et al. | |
| 2004/0219517 A1 | 11/2004 | Ecker et al. | |
| 2005/0130196 A1 | 6/2005 | Hofstadler | |
| 2005/0164215 A1 | 7/2005 | Hofstadler | |
| 2005/0266397 A1 | 12/2005 | Ecker et al. | |
| 2005/0270191 A1 | 12/2005 | Hofstadler | |
| 2006/0121520 A1 | 6/2006 | Ecker et al. | |
| 2006/0205040 A1 | 9/2006 | Sampath et al. | |
| 2006/0240412 A1 | 10/2006 | Hall | |
| 2006/0259249 A1 | 11/2006 | Sampath et al. | |
| 2006/0275749 A1 | 12/2006 | Sampath et al. | |
| 2006/0275788 A1 | 12/2006 | Ecker et al. | |
| 2007/0264639 A1 | 11/2007 | Zenser et al. | |
| 2009/0280471 A1 * | 11/2009 | Ecker et al. | 435/5 |

OTHER PUBLICATIONS

Li et al., Journal of Virological Methods, vol. 142, pp. 218-222, 2007.*
Baldwin et al. Nuclear rDNA Evidence for Major Lineages of Helenioid Heliantheae (Compositae); Systematic Botany, 2002, vol. 27(1). p. 161-198.
Schilling, E.E., et al. A revised classification of subtribe Helianthinae (Asteraceae: Heliantheae). I. Basal lineages, Botanical Journal of the Linnean Society, 2002, vol. 140, pp. 65-76.
Lowe T., et al., A computer program for selection of oligonucleotide primers for polymerase chain reactions, Nucleic acid research, 1990, vol. 18(7), pp. 1757-1761.
U.S. Appl. No. 12/058,353, Office Action dated Oct. 7, 2009, 13 pages.
U.S. Appl. No. 12/058,353, Search Reports cited in Office Action dated Oct. 7, 2009, 13 pages.
U.S. Appl. No. 12/058,353, Response to Office Action filed Feb. 8, 2010, 13 pages.
Aceto, S., et al.; Phylogeny and evolution of Orchis and allied genera based on ITS DNA variation: morphological gaps and molecular continuity; Mol Phylogenet Evol., Oct. 1999;13(1); pp. 67-76.
Ainouche, M.L. & Bayer, R.J. "On the origins of the tetraploid Bromus species (section Bromus, Poaceae): insights from internal transcribed spacer sequences of nuclear ribosomal DNA" Genome, Oct. 1997; 40(5); pp. 730-743.
Bains, W. "DNA Sequencing by Mass Spectrometry. Outline of a Potential Future Application" Chimicaoggi. vol. 9, No. 10, Oct. 1991; pp. 13-16, 1991.
Binns, S.E., et al. "A taxonomic revision of *Echinacea* (Asteraceae: Heliantheae)" Syst. Bot. 2002, vol. 27, pp. 610-632.
Bobowski, B.R., et al. "Identification of roots of woody species using polymerase chain reaction (PCR) and restriction fragment length polymorphism (RFLP) analysis" Mol Ecol. Mar. 1999; 8(3); pp. 485-491.
Chen, C.H. Winston, et al.; Laser Desorption Mass Spectrometry for Fast DNA Sequencing; U.S. Department of Energy, DOE Human Genome Program Contractor-Grantee Workshop IV, 1994; retrieved from http://www.ornl.gov/sci/techresources/Human_Genome/publicat/94SANTA/sequencing/chen.shtml.
Chen, C.H. Winston, et al.; Laser Desorption Mass Spectrometry for DNA Sequencing and Analysis; Session K14—Nucleic Acids; MIXED session, Tuesday afternoon, Mar. 17, 1998, Los Angeles Convention Center; retreived from http://flux.aps.org/meetings/YR98/BAPSMAR98/abs/S2000012.html.
Chen, C.H., et al.; Laser Desorption Mass Spectrometry for high throughput DNA analysis and its applications; 1999; retrieved from http://www.osti.gov/bridge/servlets/purl/3655-nx94bv/webviewable/3655.pdf.
Chen, C.H. Winston, et al.; Laser Desorption Mass Spectrometry for DNA Sequencing and Analysis; DOE Human Genome Program Contractor-Grantee Workshop VIII Jan. 12-16, 1999 Oakland, CA; retrieved from http://www.ornl.gov/sci/techresources/Human_Genome/publicat/99santa/45.html.
Chen, C.H. Winston, et al.; Laser mass sepctrometry for DNA sequencing, disease diagnosis, and fingerprinting; SPIE vol. 2985; 1997; pp. 70-81.

(Continued)

*Primary Examiner* — Gary Benzion
*Assistant Examiner* — Cynthia Wilder
(74) *Attorney, Agent, or Firm* — Tracy Jong Law Firm; Tracy P. Jong

(57) ABSTRACT

An improved method for rapid identification of microorganisms is disclosed, along with sequences of PCR primers optimized for this purpose. The primers are designed based on information analysis of sequences from a large number of organism to amplify certain segments of genomic DNA whose sequences are unique among different organisms. The PCR products are compared with a DNA sequence database to obtain the identity of the microorganisms. This approach provides an accurate and fast identification and taxonomic assignment of microbial species.

24 Claims, 5 Drawing Sheets

OTHER PUBLICATIONS

Emshwiller, E. & Doyle, J.J.; Origins of domestication and polyploidy in oca (*Oxalis tuberosa*: Oxalidaceae). 2. Chloroplast expressed glutamine synthetase data. American Journal of Botany 89(7), 2002; pp. 1042-1056.

Emshwiller, E. & Doyle, J.J; Origins of domestication and polyploidy in oca (*Oxalis tuberosa*: Oxalidaceae): nrDNA ITS data. American Journal of Botany 85(7); 1998; pp. 975-985.

Ecker, D.J., et al. "Rapid identification and strain-typing of respiratory pathogens for epidemic surveillance" Proc Natl Acad Sci USA 102(22); May 2005, pp. 8012-8017.

Ecker, D.J., et al. "The Microbial Rosetta Stone Database: a compilation of global and emerging infectious microorganisms and bioterrorist threat agents" BMC Microbio15(1):19, (2005); 17 pages.

Ecker, J.A., et al. "Identification of Acinetobacter species and genotyping of Acinetobacter baumannii by multilocus PCR and mass spectrometry" J Clin Microbio144(8), (2006), pp. 2921-2932.

Edwards, J.R., et al; Mass-Spectrometry DNA Sequencing; Mutation Research 573 (2005) 3-12.

Edwards, J.R. et al.; DNA sequencing using biotinylated dideoxynucleotides and mass spectrometry; Nucleic Acids Research 2001, vol. 69, No. 21, e104; pp. 1-6.

Fitzgerald, M.C. et al; The Analysis of Mock DNA Sequencing Reactions Using Matrix-assisted Laser Desporption/Ionization Mass Spectrometry; Rapid Communications in Mass Spectrometry, vol. 7; 895-897 (1993).

Francisco-Ortega J., et al., Internal Transcribed Spacer Sequence Phylogeny of *Crambe* L. (Brassicaceae): Molecular Data Reveal Two Old World Disjunctions; Mol Phylogenet Evol., Apr. 1999; 11(3); pp. 361-380.

Hall, T.A. et al.; Base composition analysis of human mitochondrial DNA using electrospray ionization mass spectrometry: a novel tool for the identification and differentiation of humans; Analytical Biochem. 344 (2005); pp. 53-69.

Herwig, R., et al.; Information theoretical probe selection for hybridisation experiments; vol. 16, No. 10, 2000, pp. 890-898.

Hujer, K.M. et al. "Analysis of antibiotic resistance genes in multidrug-resistant Acinetobacter sp. isolates from military and civilian patients treated at the WalterReed Army Medical Center" Antimicrob Agents Chemother 50(12), (2006), pp. 114-123.

Jacobson, K.B. et al.; Applications of mass spectrometry to DNA sequencing; GATA 8(8), 1991; pp. 223-229.

Jupe, E.R. & Zimmer, E.A.; Unmethylated regions in the intergenic spacer of maize and teosinte ribosomol RNA genes; Plant Mol Biol.; Mar. 1990;14(3); pp. 333-347.

Kirpekar, F., et al.; DNA sequence analysis my MALDI mass spectrometry; Nucleic Acids Research, 1998, vol. 26, No. 11; pp. 2554-2559.

Kim, D.H. et al.; Genetic diversity of *Echinacea* species based upon amplified fragment length polymorphism markers. Genome, Feb. 2004; 47(1); pp. 102-111.

Koopman, W.J.M., et al., Phylogenetic Relationships Among *Lactuca* (Asteraceae) Species and Related Genera Based on ITS-1 DNA Sequences; Am. J. Bot. 85(11), 1998; pp. 1517-1530.

Koster, H. et al.; A strategy for rapid and efficient DNA sequencing by mass spectrometry; Nature Biotech; vol. 14, Sep. 1996; pp. 1123-1128.

Krause, J. et al.; High Resolution Characterization of DNA Fragment Ions Produced by Ultraviolet Matrix-Assisted Laser Desporption/Ionization Using Linear and Reflecting Time-of-Flight Mass Spectrometry; J. Am. Soc. Mass Spectrom., 1999, 10, pp. 423-429.

Lesnik et al. (2005) "Identification of conserved regulatory RNA structures in prokaryotic metabolic pathway genes" Biosystems 80(2):145-54.

Little, D.P., et al.; Rapid Sequencing of Oligonucleotides by High-Resolution Mass Spectrometry; J. Am Chem Soc. 116, 1994, pp. 4893-4897.

Little, D.P. & McLafferty, F.W.; Sequencing 50-mer DNAs Using Electrospray Tandem Mass Spectrometry and Complementary Fragmentation Methods; J. Am Chem Soc. 117, 1995, pp. 6783-6784.

Little, D.P., et al.; Sequencing Information from 42—108-mer DNAs (Complete for a 50-mer) by Tandem Mass Spectrometry; J. Am Chem Soc. 118, 1996, pp. 9352-9359.

Little, D.P., et al.; Verification of 50- 100-mer DNA and RNA sequences with high resolution mass spectrometry; Proc. Natl. Acad. Sci. USA vol. 92, Mar. 1995, pp. 2318-2322.

Liu, J.-S. & Schardl, C.L.; A conserved sequence in internal transcribed spacer 1 of plant nuclear rRNA genes; Plant Mol Biol., Oct. 1994 vol. 26, No. 2, pp. 775-778.

Martin, W.J.; New technologies for large-genome sequencing; Genome vol. 31, 1989; pp. 1073-1080.

Murray, K.K.; Special Feature: Tutorial—DNA Sequencing by Mass Spectrometry; Journal of Mass Spectrometry; vol. 31, 1996; pp. 1203-1215.

Nelson, R.W., et al.; Volitization of High Molecular Weight DNA by Pulsed Laser Ablation of Frozen Aqueous Solutions; Science vol. 246; Dec. 1989; pp. 1585-1587.

Ni, J. et al.; "Interpretation of Oligonucleotide Mass Spectra for Determination of Sequence Using Electrospray Ionization and Tandem Mass Spectrometry"; Anal. Chem 1996, vol. 68, No. 13; pp. 1989-1999.

Nordhoff, E. et al.; Direct Mass Spectrometric Sequencing of Low-picomole Amounts of Oligodeoxynucleotides with up to 21 Bases by Matrix-assisted Laser Desorption/Ionization Mass Spectrometry; Journal of Mass Spectrometry; vol. 30 (1995); pp. 99-112.

Parr, G.R., et al; "Matrix-Assisted Laser Desorption/Ionization Mass Spectrometry of Synthetic Oligodeoxyribonucleotides", Rapid Communications in Mass Spectrometry, 1992, 6, 369-372.

Reamon-Buttner, S.M., et al., AFLPs represent highly repetitive sequences in *Asparagus officinalis* L. C. Chromosome Res.; 1999, vol. 7 No. 4; pp. 297-304.

Rogan P.K., et al.;Visual Display of Sequence Conservation as an Aid to Taxonomic Classification Using PCR Amplification; In: Visualizing Biological Information, CA Pickover (ed). World Scientific, River Edge NJ, 1995; pp. 21-32.

Roskey, M.T., et al.; DNA sequencing by delayed extraction-matrix-assisted laser desporption/ionization time of flight mass spectrometry; Proc Natl. Acad. Sci. USA, vol. 93, May 1996, pp. 4724-4729.

Sakai, R.K., et al.; Enzymatic amplification of beta-globin genomic sequences and restriction site analysis for diagnosis of sickle cell anemia; Science 20; Dec. 1985; pp. 1350-1354.

Sampath, R. et al. (2005) Rapid identification of emerging Infectious agents Using PCR and Electrospray Ionization Mass Spectrometry; Ann. N.Y. Acad. Sci. 1102 (2007); pp. 109-120.

Sampath, R. et al. "Rapid identification of emerging pathogens: coronavirus" Emerg Infect Dis (2005) 11(3): 373-9.

Sanger F, et al. "DNA sequencing with chain-terminating inhibitors." Proc Natl Acad Sci USA. 1977 74 (12); pp. 5463-5467.

Schneider, T.D. & Stephens, R.M.; Sequence logos: a new way to display consensus sequences; Nucleic Acids Research; vol. 18, No. 20, 1990, pp. 6097-6100.

Schneider, T.D., et al.; Information Content of Binding Sites on Nucleotide Sequences; J. Mol. Biol. (1986) 188; pp. 415-431.

Seth, P.P.; et al; Discovery of a New Class of RNA-Binding Small Molecules for the Hepatitis C Virus: Internal Ribosome Entry Site IIA Subdomain; J. Med. Chem. 48 (2005); pp. 7099-7102.

Siudzak, G. "The emergence of mass spectrometry in biochemical research" Proc. Natl Acad Sci USA, vol. 91, Nov. 1994, pp. 11290-11297.

Skinner, K.A.; Bacterial contaminants of fuel ethanol production; J. Ind. Microbiol. Biotechnol. vol. 31, 2004; pp. 401-408.

Soltis, P.S. & Soltis, D.E.; The role of genetic and genomic attributes in the success of polyploids Proc Natl Acad Sci USA, Jun. 2000; 97(13); pp. 7051-7057.

Stimpel, M., et al.; Macrophage Acivation and Induction of Macrophage Cytotoxicity by Purified Polysaccharide Fractions from the Plant *Echinecea purpurea*; Infection and Immunity, vol. 46, No. 3, Dec. 1984; pp. 845-849.

Tang, K., et al., Mass-Spectrometry of Laser-Desorbed Oligonucleotides. Rapid Communications in Mass Spectrometry, 1992. 6(6): p. 365-368.

Tang, W., et al.; Controlling DNA Fragmentation in MALDI-MS by Chemical Modification; Anal. Chem., vol. 69, 1997, pp. 302-312.

Tang K, et al.; Matrix-assisted laser desorption/ionization mass spectrometry of immobilized duplex DNA probes. Nucleic Acids Res. Aug. 25, 1995; 23(16); pp. 3126-3131.

Tooley, P.W., et al.; Phylogenetic Inference Based on Information Theory-Based PCR Amplification; J. Phytopathology, vol. 146; (1998) pp. 427-430.

Van Der Stappen, J., et al.; Sequencing of the Internal transcribed spacer region ITS1 as a molecular tool detecting variation in the *Stylosanthes gulanenis* species complex; Theor. Appl. Genet. 96, 1998, pp. 869-877.

Van Ert et al. (2004) "Mass spectrometry provides accurate characterization of two genetic marker types in Bacillus anthracis" Biotechnigues 37(4):642-4.

Whiting, M., et al.; Detection of *pediococcus* spp. in Brewing Yeast by a Rapid Immunoassy; Appl. Environ. Microbiol., vol. 58, No. 2, Feb. 1992; pp. 713-716.

Woese, C.R.; Bacterial Evolution; Microbiol Rev. Jun. 1987 51(2); pp. 221-271.

Wu, K.J., et al.; Time-of-Flight Mass Spectrometry of Underivatized Single-Stranded DNA Oligomers by Matrix-Assisted Laser Desorption, Anal. Chem., 1994, pp. 1637-1645.

Maxam, A.M. & Gilbert, W., "Sequencing end-labeled DNA with base-specific chemical cleavages." Methods Enzymol.; ed. Grossman & Moldave; 1980 vol. 65(1):499-560.

Colin Ohrt, Laura Mirabelli-Primdahl, Sornchai Looareesuwan, Polrat Wilairatana, Douglas Walsh, Kevin C. Kain, Determination of Failure of Treatment of Plasmodium falciparum Infection by Using Polymerase Chain Reaction Single-Strand Conformational Polymorphism Fingerprinting, Clinical Infectious Diseases, Apr. 28, 1999, 847-852, Infectious Diseases Society of America, Arlington, US.

* cited by examiner

```
                          SEQUENCE LISTING

<160> NUMBER OF SEQ ID NOS: 6

<210> SEQ ID NO 1
<211> LENGTH: 17
<212> TYPE: DNA
<213> ORGANISM: Artificial
<220> FEATURE:
<223> OTHER INFORMATION: Synthetic degenerate oligonucleotide derived
      from analysis of information from a multi-sequence alignment of
      ribosomal RNA sequences. Degenerate positions are represented by
      symbols other than a, t, g and c.
<220> FEATURE:
<221> NAME/KEY: misc_feature
<222> LOCATION: (1)..(17)
<223> OTHER INFORMATION: Representation of nucleotides and their
      proportionate frequency at each degenerate position are defined as
      follows and in the application: r=a/g, y=c/t, m=a/c, k=g/t, w=a/t,
      s=c/g, b=t/g/c, d=a/t/g, h=a/t/c, v=a/g/c, n=a/t/g/c.

<400> SEQUENCE: 1
gtgbcagcng ynbyggt                                                 17

<210> SEQ ID NO 2
<211> LENGTH: 21
<212> TYPE: DNA
<213> ORGANISM: Artificial
<220> FEATURE:
<223> OTHER INFORMATION: Synthetic degenerate oligonucleotide derived
      from analysis of information from a multi-sequence alignment of
      ribosomal RNA sequences. Degenerate positions are represented by
      symbols other than a, t, g and c.
<220> FEATURE:
<221> NAME/KEY: misc_feature
<222> LOCATION: (1)..(21)
<223> OTHER INFORMATION: Representation of nucleotides and their
      proportionate frequency at each degenerate position are defined as
      follows and in the application: r=a/g, y=c/t, m=a/c, k=g/t, w=a/t,
      s=c/g, b=t/g/c, d=a/t/g, h=a/t/c, v=a/g/c, n=a/t/g/c.

<400> SEQUENCE: 2
ccmdhcwath hnytkvrstw k                                            21

<210> SEQ ID NO 3
<211> LENGTH: 18
<212> TYPE: DNA
<213> ORGANISM: Artificial
<220> FEATURE:
<223> OTHER INFORMATION: Synthetic degenerate oligonucleotide derived
      from analysis of information from a multi-sequence alignment of
      ribosomal RNA sequences. Degenerate positions are represented by
      symbols other than a, t, g and c.
<220> FEATURE:
<221> NAME/KEY: misc_feature
<222> LOCATION: (1)..(18)
<223> OTHER INFORMATION: Representation of nucleotides and their
      proportionate frequency at each degenerate position are defined as
      follows and in the application: r=a/g, y=c/t, m=a/c, k=g/t, w=a/t,
      s=c/g, b=t/g/c, d=a/t/g, h=a/t/c, v=a/g/c, n=a/t/g/c.

<400> SEQUENCE: 3
nbkhhwrbbn nnnaacga                                                18

<210> SEQ ID NO 4
<211> LENGTH: 21
<212> TYPE: DNA
<213> ORGANISM: Artificial
```

```
-continued

<220> FEATURE:
<223> OTHER INFORMATION: Synthetic degenerate oligonucleotide derived
      from analysis of information from a multi-sequence alignment of
      ribosomal RNA sequences. Degenerate positions are represented by
      symbols other than a, t, g and c.
<220> FEATURE:
<221> NAME/KEY: misc_feature
<222> LOCATION: (1)..(21)
<223> OTHER INFORMATION: Representation of nucleotides and their
      proportionate frequency at each degenerate position are defined as
      follows and in the application: r=a/g, y=c/t, m=a/c, k=g/t, w=a/t,
      s=c/g, b=t/g/c, d=a/t/g, h=a/t/c, v=a/g/c, n=a/t/g/c.

<400> SEQUENCE: 4
cahdgyadbn yghktshncc c                                             21

<210> SEQ ID NO 5
<211> LENGTH: 18
<212> TYPE: DNA
<213> ORGANISM: Artificial
<220> FEATURE:
<223> OTHER INFORMATION: Synthetic degenerate oligonucleotide derived
      from analysis of information from a multi-sequence alignment of
      ribosomal RNA sequences. Degenerate positions are represented by
      symbols other than a, t, g and c.
<220> FEATURE:
<221> NAME/KEY: misc_feature
<222> LOCATION: (1)..(18)
<223> OTHER INFORMATION: Representation of nucleotides and their
      proportionate frequency at each degenerate position are defined as
      follows and in the application: r=a/g, y=c/t, m=a/c, k=g/t, w=a/t,
      s=c/g, b=t/g/c, d=a/t/g, h=a/t/c, v=a/g/c, n=a/t/g/c.

<400> SEQUENCE: 5
nbkhhwrbbn nnnaacga                                                 18

<210> SEQ ID NO 6
<211> LENGTH: 20
<212> TYPE: DNA
<213> ORGANISM: Artificial
<220> FEATURE:
<223> OTHER INFORMATION: Synthetic degenerate oligonucleotide derived
      from analysis of information from a multi-sequence alignment of
      ribosomal RNA sequences. Degenerate positions are represented by
      symbols other than a, t, g and c.
<220> FEATURE:
<221> NAME/KEY: misc_feature
<222> LOCATION: (1)..(20)
<223> OTHER INFORMATION: Representation of nucleotides and their
      proportionate frequency at each degenerate position are defined as
      follows and in the application: r=a/g, y=c/t, m=a/c, k=g/t, w=a/t,
      s=c/g, b=t/g/c, d=a/t/g, h=a/t/c, v=a/g/c, n=a/t/g/c.

<400> SEQUENCE: 6
dbbvhvgrss vgtkwgtrca                                               20
```

RAPID AND COMPREHENSIVE IDENTIFICATION OF PROKARYOTIC ORGANISMS

RELATED APPLICATIONS

This application claims priority of U.S. Provisional Application No. 60/886,595, filed Jan. 25, 2007, the content of which is hereby incorporated into this application by reference.

SEQUENCE LISTING

This application is accompanied by a sequence listing that accurately reproduces the sequences described herein.

BACKGROUND

1. Field of the Invention

The present disclosure pertains to methods for rapid detection and identification of microorganisms. More particularly, the disclosure relates to identification of prokaryotic organisms through molecular characterization of their genetic materials, such as DNA or RNA.

2. Description of Related Art

Microorganisms, such as bacteria, are a major cause of infections in higher mammals, including human. Although some infections may be treated without knowing the identity of the infectious agent, it is sometimes important for clinicians to know the identity of the infectious agent in order to prescribe the most effective treatment for the infection. This is particularly true for bacterial infections because different species of bacteria may respond differently to the same antibiotics.

In addition to their role as pathogens, prokaryotic microorganisms also play an important role in many industrial areas. Beer spoilage caused by bacteria has been a chronic problem for the beer industry. Prokaryotes are often found in various environmental contamination sites, and knowledge of the identity of these organisms can be useful for remediation. Identification of these prokaryotes may be instrumental for solving these problems.

Conventional methods for classification and identification of a microorganism require culturing of the microorganism, and typically rely on morphological or biochemical characteristics of the organism. The culturing step may delay identification, which can have consequences on the effectiveness of appropriate treatment, and may also increase exposure of laboratory workers to pathogens. The delay in identification may in turn increase the chances that the pathogens may be spread to others while awaiting lab test results. Moreover, the test results may be skewed when multiple microorganisms are present and the growth of one microorganisms inhibits the growth of others in the laboratory environment. There is therefore a need for a method which may rapidly identify the organisms without requiring culturing of the microorganisms in a laboratory environment.

Nucleic acid sequences of homologous genes have been used to distinguish different species. The differences in nucleotide usage, frequency and arrangement may indicate the degree to which different organisms have diverged from a common ancestor. U.S. Pat. No. 5,849,492 discloses a method for rapid identification of species based on taxonomically variable set of orthologous sequences, including ribosomal RNA genes. More specifically, the '492 patent teaches a process whereby the sequences of ribosomal RNA molecules may be used to identify genetic differences between species. An information theory-based sequence analysis is used to select sequences in the homologous 16S ribosomal RNA genes (16S rDNA) for DNA amplification. The '492 patent discloses a pair of primers amplifying orthologous ribosomal gene or RNA sequences that are selected using information theory-based methods that detect gene regions revealing sequences that are maximally divergent among multiple species, which make these primers and amplicons useful for identifying prokaryotes. However, there are limitations to the sensitivity and specificity of this method, because computational analysis in the '492 patent was based on a multiple alignment of 16S rDNA sequences from only 55 prokaryotic organisms.

SUMMARY

It is hereby disclosed a methodology by which nucleic acid amplification is used to identify microorganisms without the need to culture the infectious agents. A single DNA amplification and sequencing assay (omnibus PCR) have been developed which may accurately identify a wide spectrum of infectious disease agents in vitro within a few hours after the specimen is collected.

U.S. Pat. No. 5,849,492 describes methods and primer sequences for 16S rDNA and 28S rDNA for identification of prokaryotic and eukaryotic organisms, respectively. The teachings of the '492 patent are hereby expressly incorporated into this disclosure by reference.

The methodology disclosed here is an improvement upon the technology described in the '492 patent. The present disclosure uses a more comprehensive set of orthologous gene sequences derived from a more diverse and larger set of taxa than those described in the '492 patent to design primers that are capable of amplifying the 16S rDNA from a broader spectrum of prokaryotic species. As a result, a wider spectrum of organisms may be identified with the presently disclosed primers and methodology.

Since almost all organisms employ ribosomes to synthesize proteins, ribosomal subunits have been structurally and functionally conserved throughout the eons. Thus, ribosomal RNAs from widely differing species may differ in a small number of nucleotides. These limited sequence variations may be used to characterize the evolutionary or phylogenetic relationships between the organisms and to identify a specific organism. Briefly, information (in bits) may be used to precisely quantify both the similarities and divergence among 16S gene sequences, because information measures the number of choices between two equally likely possibilities (Schneider et al., *J. Mol. Biol.* 188: 415-431, 1986). Variable positions in a multiply aligned set of 16S rDNA sequences approach zero bits and homologous or highly conserved sequences have nearly two bits in a sequence logo (Stephens & Schneider, *Nucl. Acids Res.* 18: 6097-6100, 1990), which displays the average information content ($R_{sequence}$) and frequencies of each nucleotide at each position.

The average information in bits of a related set of sequences, $R_{sequence}$, represents the total sequence conservation:

$$R_{sequence} = 2 - \left[ -\sum_{b=a}^{t} f(b, l)\log 2 f(b, l) + e(n(l)) \right] \qquad \text{I}$$

f(b,l) is the frequency of each base b at position l,
e(n(l)) is a correction for the small sample size n at position l.

A sequence logo may then be constructed based on the $R_{sequence}$ to locate segments consisting of sequences with low information content flanked on either side by sequences with high information content.

Three different sets of PCR primers based on the 16S rDNA sequences from more than 2000 species were developed using the instant method and tested using both purified DNA from 100 different bacterial pathogens that are commonly found in hospital laboratories and with 299 uncultured clinical specimens of various types from patients with suspected bacterial infections. Primer set A (coordinates 931-1462 of the 16S rDNA sequence logo) may be used to amplify segments of the 16S rDNA product from prokaryotes. The other two sets of primers, B and C, which amplify sequences corresponding to coordinates 1819-2370 and 1819-2599 of the sequence logo, respectively, may be employed to confirm or refine the amplification results obtained using primer set A. 90% of the prokaryotic organisms identified with primer set A can be confirmed and in some instances, refined with primer sets B and C.

An improved method is also described for identifying more than one microorganisms present at the same infection site. Using the PCR and sequencing methodology described above, there may be instances where the sequence is not readable because there are multiple peaks at several locations in the sequence. To eliminate this problem, a constant denaturing gel electrophoresis (CDGE) protocol has been developed, which allows DNA to be separated on the basis of sequence composition and duplex stability in a vertical polyacrylamide gel.

The separated PCR products may be characterized based upon properties selected from the group consisting of nucleotide composition, base composition, nucleotide sequence, DNA structure, mass ratio of the DNA molecules or fragments derived therefrom, chemical reactivity of the DNA molecules, binding properties to other DNA molecules or proteins, thermal stability, and combination thereof. In another aspect, multiple PCR products may be separated and sequenced simultaneously using mass spectrometry.

In summary, it is disclosed here a number of oligonucleotides useful for taxonomic assignment of unknown species as well as for identification of clinically important pathogens. The method may generally include the following steps:
(a) searching for a divergent segment of DNA with low average information content determined quantitatively surrounded by two conserved segments of said DNA with high average information content determined quantitatively;
(b) designing primers for PCR amplification of said divergent segment by constructing a sequence logo for said DNA such that said primers contain a set of sequences present in said sequence logo that encompass the nucleotide variability of said conserved segments, which primers can anneal to said conserved segments;
(c) amplifying said divergent segment of DNA by PCR technique using said primers to obtain PCR products;
(d) separating said PCR products based on the difference in sequences; and
(e) characterizing the separated PCR products based upon properties selected from the group consisting of nucleotide composition, base composition, nucleotide sequence, DNA structure, mass ratio of the DNA molecules or fragments derived therefrom, chemical reactivity of the DNA molecules, binding properties to other DNA molecules or proteins, thermal stability, and combination thereof.

In the case of pathogen identification, clinical samples are preferably processed to obtain a solution or suspension containing the DNA or RNA from the pathogens. Clinical samples may include, for example, blood, bone marrow aspirate, synovial fluid, biopsied samples, mucus, stool, urine, etc. In another aspect, the samples may be processed to remove certain impurities that may impede the PCR reactions, such as red blood cells, salts, etc. At times, sample concentration or dilution may be needed to optimize the PCR condition. In yet another aspect, the method may further include a step wherein the existence of a pathological condition or a disease in an individual is determined base upon the identity of the organism obtained in steps (a)-(e) described above.

For purpose of this disclosure, pathogens may include bacteria, viruses, fungi and other clinically significant microorganisms generally known to the medical community. Without limiting the scope of this invention, the method disclosed herein may be applicable to many organisms, including but not limited to, Acinetobacter, Actinobacillus, Actinomyces pyogenes, Actinomyces pyogenes, Aeromonas hydrophilia, Alcaligenes fecalis, Aligella urethralis, Alteromonas putriaciens, Alteromonas putrifuciens, Bacteriodes distasonis, Bacteriodes fragila, Bacteriodes melaminogenicus, Bacteriodes ovatus, Bacteriodes thetaiomicion, Bacteriodes uniformis, Campylobacter, Candida albicans, Capnocytophaga, CDC group Ivc, Chlamydia trachomatis, Citrobacter fruendii, Clostridium difficle, Clostridium histolyticum, Clostridium perfingens, Clostridium septicum, Clostridium sordelli, Clostridium sporogenes, Corynebacterium diptheria, Corynebacterium pseudodoi., E. coli, E. coli 0157-H7, E. coli-βlactamase positive, Enterobacter aerogenes, Enterobacter cloecae, Enterobacter fecalis, Eubacterium lentum, Flavobacterium meningiosepticum, Fusobacterium, Fusobacterium miningio, Haemophilia parainfluenza, Haemophilis influenza, Haemophilus aphrophilus, Klebsiella oxytoca, Klebsiella pneumonia, Klebsiella rhinoscleromatis, Legionella micdliea, Legionella pneumophilia, Leuconostoc lactic, Leuconostoc mesanteriodas, Listeria murrayi, Mima, Mycobacterium avium intracellulari, Mycobacterium flavescens, Mycobacterium gordoniae, Mycobacterium terra group, Mycobacterium tuberculoses, Neisseria cinerea, Neisseria gonorrhea, Neisseria lactamica, Neisseria meningiditis, Neisseria sicca, Nocardia brasiliensis, Pasteurella multocida, Proteus mirabilis, Proteus vulgaris, Pseudomonas cepatia (strain I), Pseudomonas cepatia (strain II), Salmonella cholerasuis, Salmonella dublin, Salmonella muenchen, Salmonella paratyphi, Salmonella typhimurium, Serratia oderifera, Shigella boydii, Shigella dysenteriae, Shigella felxneri, Shigella sonneri, Staphylococcus aureus, Staphylococcus epi., Staphylococcus saphrophy, Streptococcus alpha, Streptococcus beta (Group C), Streptococcus beta (Group F), Streptococcus bovis, Streptococcus fecalis, Streptococcus Group B, Streptococcus mitis, Streptococcus mutans, Streptococcus pneumonia, Torulopsis globrata, Treponema denticola, Treponema pallidum, Treponema pertenue, Treponema phagedenis, Treponema refrigens, Vibro paruhen, and Yersinia enterolitica. For certain microorganisms that have RNA exclusively as their genetic materials, reverse transcription may be performed before subjecting the samples to PCR as described in Step (c).

DETAILED DESCRIPTION

Both the similarities and differences between microorganisms may be used to obtain the identity of these organisms. Morphological and biochemical properties have been used to differentiate among organisms, however, these methods can be time consuming and can be inaccurate, and if culturing conditions are not correct, may fail to identify the organism that is present in a specimen. According to the present disclosure, nucleic acid sequences of homologous genes in different species may reveal the identity of infectious agents. The frequency and arrangement of nucleotide differences indicate the degree to which two organisms have diverged from a common ancestor. In a preferred embodiment, the sequences of ribosomal DNA may be used to identify genetic differences between bacterial species.

In order to ensure that the widest spectrum of organisms may be identified, it is desirable to apply the information theory-based sequence analysis to a greatest possible number of species to select for sequences in the homologous 16S ribosomal RNA genes (16S rDNA) for DNA amplification. In one embodiment, full length 16S rDNA sequences from a set of bacterial species (2184 organisms obtained from Genbank v88; National Library of Medicine) having the broadest possible taxonomic distribution are used to design amplification experiments (Saiki et al., *Science* 230: 1350-1354, 1985).

The total information content at each position is the basis for selecting phylogenetically-informative regions flanked by >18 bp segments showing sufficient sequence conservation to be used as primers for the PCR amplification reaction. The ratio of the number of bits of each nucleotide at each position to the total number of bits at that site may determine the proportion of a particular nucleotide at degenerate sites in the oligonucleotide primer. A ratio of 0.001 may be taken as the minimum proportion required to include this nucleotide in a degenerate site (see below). Otherwise, the primer may be designed to be homogeneous at that position.

A sequence logo may be used to locate several segments consisting of sequences with low information (>100 nucleotides, average $R_{sequence}=0.2$) content flanked on either side by sequences with high information content and tested experimentally (Rogan et al., 1995; Tooley P W, Salvo J J, Schneider T D, Rogan P K: Phylogenetic inference using information theory-based PCR amplification. J Phytopathology, 146(8-9): 427-430, 1998).

Figure 1:
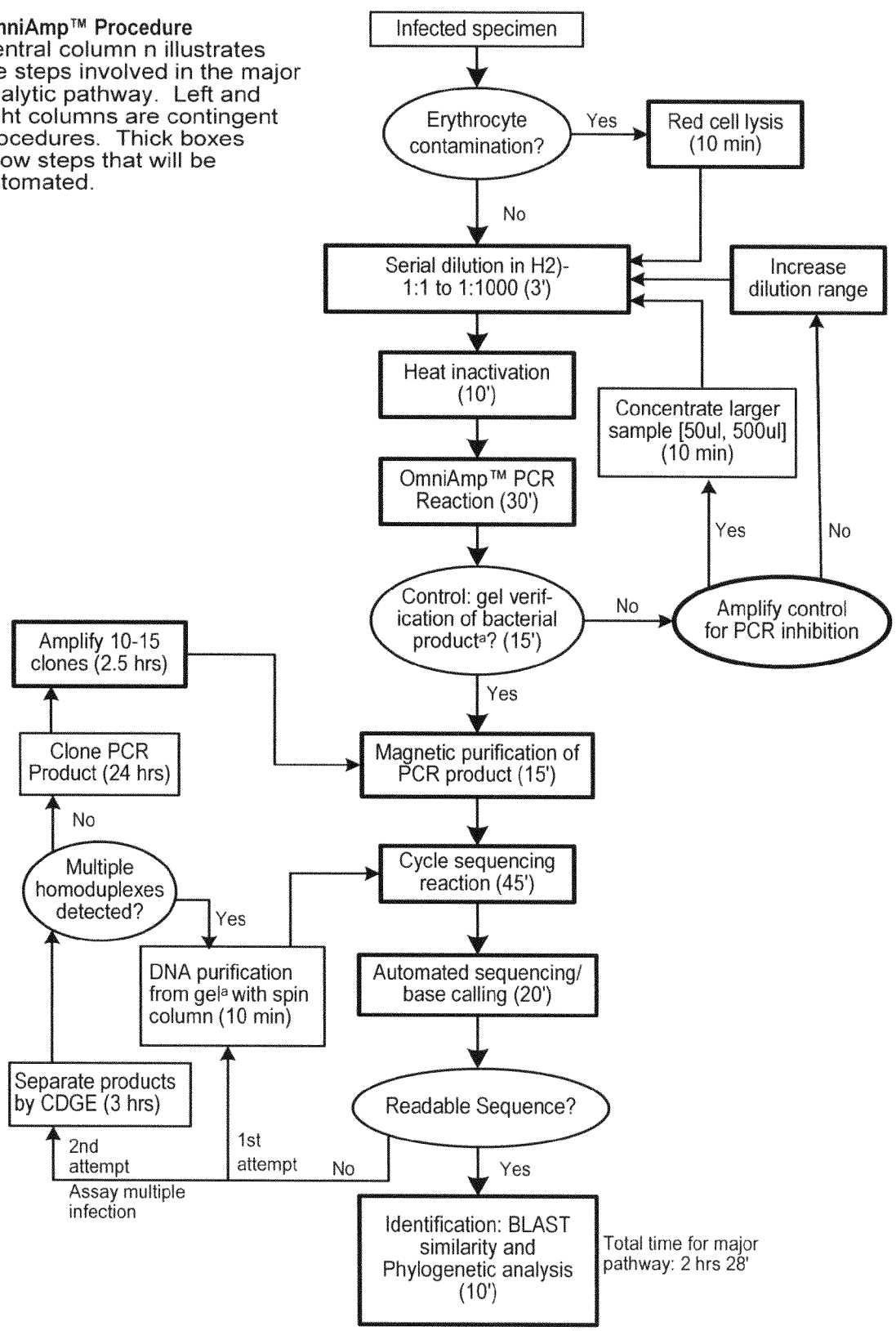
FIG. 1 is a flow chart showing the steps of the OmniAmp procedure.

FIG. 1 illustrates a typical process for identifying unknown species in a sample. The main (central column) and contingency (left and right columns) procedures are all shown in the figure. The contingency procedure is invoked only if the main procedure does not provide the desired results at any given step. The main process may be automated at several steps, as indicated by the boxes with boldtype outlines. A laboratory robot and thermal cycler inside the biosafety cabinet may be used to carry out these steps. This should maximize safety and minimize errors in handling and tracking infectious specimens.

Briefly, a clinical specimen may be dispensed into a microtiter plate, and the organism(s) contained in the specimen may be killed by heat treatment. The sensitivity of detecting different organisms usually is not compromised by this method for releasing DNA. The bacterial 16S rDNA sequence may then be amplified, and the product may be purified, preferably by magnetic methods. PCR may be generally performed by following the methodology described by Mullis K B, Faloona F A, "Specific synthesis of DNA in vitro via a polymerase-catalyzed chain reaction," Methods Enzymol. 1987; 155:335-50. The purified PCR product may then be cycle sequenced (using the original amplification primers for sequencing and a set of complimentary sequencing primers derived from a high-information content interval from within the amplification product; these sequencing primers are also designed to be degenerate so as to include the respective combinations of nucleotides present and in the same frequencies that these nucleotides are observed in the multiple alignment (in this case of 2184 sequences). A contig of redundant, overlapping sequences from the complementary sequences derived from both strands of the product may be constructed from the sequences produced using the internal sequencing primers and by using the amplification primers to initiate sequencing.

The resultant consensus sequence derived from the contig may then be compared with a database containing a large collection of ribosomal sequences from a large number of organisms. The database comparison may be carried out on a local computer or remotely through a web-based tool. For example, the National Center for Biotechnology Information's (NLM) Basic Local Alignment Search Tool may be used to carry out the sequence comparison to a database of ribosomal DNA gene sequences culled from GenBank or Ribosomal Gene Database entries.

The sequences showing the greatest similarity (and one distantly related sequence) may be multiply aligned with the test sequence. The Clustal program may be used for the alignment, and several different types of phylogenetic trees may be constructed demonstrating the taxonomic relationship between the test sequence and those derived from the other organisms.

Oligonucleotide DNA primers may be designed such that both the conserved regions and the divergent DNA sequences between them may be amplified (example shown below). The 3' termini of these primers are preferably selected at positions in the sequence logo with maximal information content (as close to 2 bits as possible), so that the primer end is always complementary to any bacterial template that is found in the series of orthologous genes that is used to design them. The 5' termini and internal primer positions of each primer are more permissive for degeneracy, with frequencies of each nucleotide corresponding to those given by the information analysis. This design may increase the efficiency of amplification, allowing the orthologous 16S rDNA sequences to be obtained from a maximum number of organisms. Oligonucleotide mixtures are defined by the frequencies of each nucleotide in the sequence alignment. This feature may maximize the sensitivity without sacrificing specificity for the 16S rDNA genes because these oligonucleotides are complementary to most potential genomic targets. A limitation of this method, however, is that omnibus amplification of genes whose functions and sequences are not widely conserved throughout the prokaryotic kingdom cannot be used to identify those species in which they are not found. Therefore, preferred genes used in this invention include those which perform functions that are necessary to provide essential or fundamental cellular functions (e.g. ribosomal genes needed for protein translation, cytochrome P450-related genes, ie. cytochrome b5, needed for oxidative respiration, other housekeeping genes).

Figure 2:
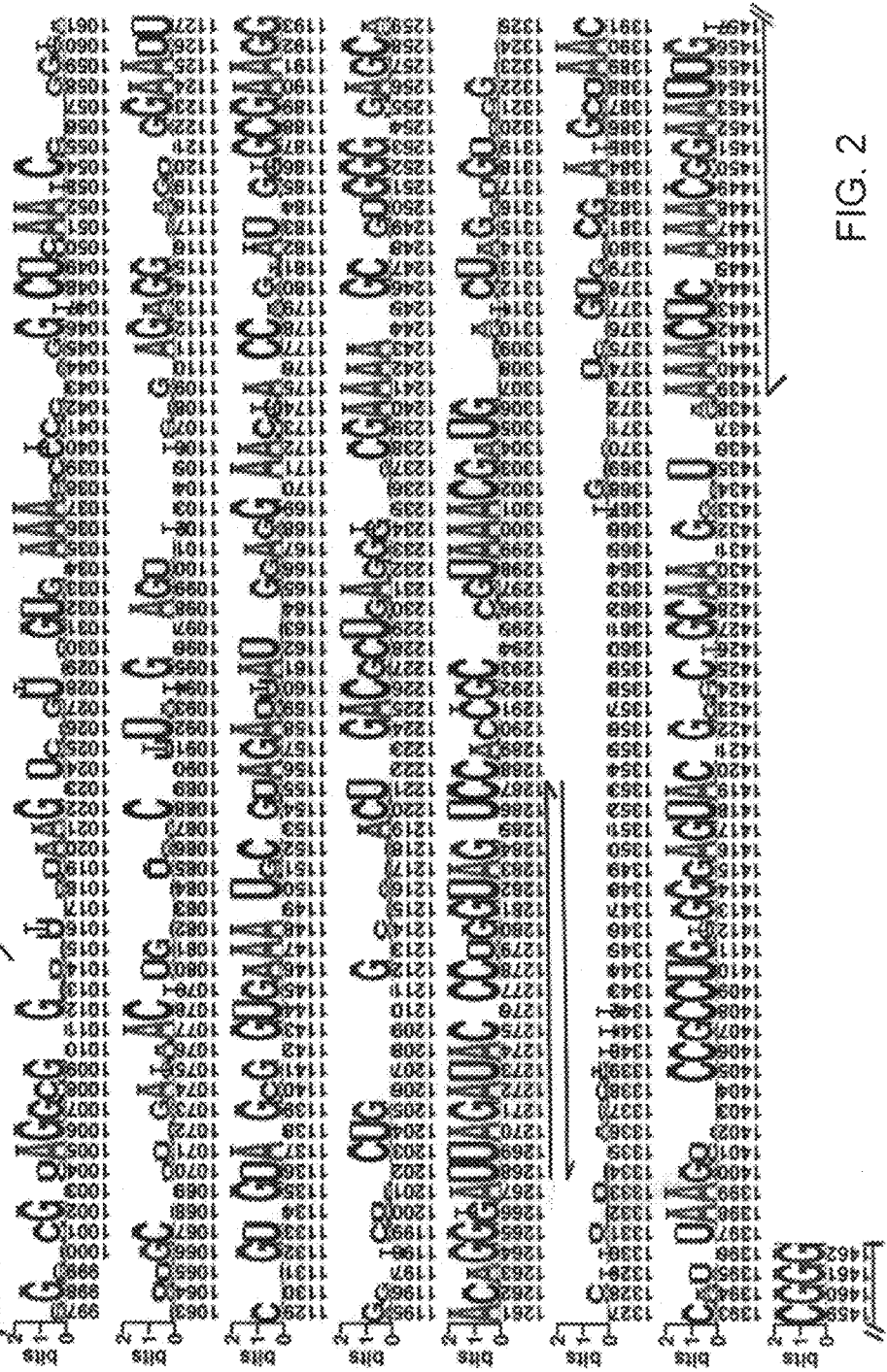
FIG. 2 shows a sequence logo constructed based on the rDNA sequences from 2184 organisms obtained from Genbank v88; National Library of Medicine.

FIG. 2 shows an example of a sequence logo constructed for the purpose of designing primers. The sequence logo indicates the sequence conservation among a multiple alignment of ribosomal small subunit 16S rRNA genes of 2251 prokaryotic species. The portion of the logo shown indicates the region used to select primer pair set A indicated in the specification. The height of each stack of letters depicts the overall conservation in bits of information at each position and the relative heights of each nucleotide correspond to the percentage of gene sequences at that position containing that nucleotide. The error bars of the computation of average information at each position are indicated at the top of each stack. The locations of the primers used for PCR amplification and DNA sequencing of the amplification products are presented using arrows (orientation corresponds to the strandedness of the sequence) below the logo at the corresponding numbered positions. The primers are named according to these coordinates. Note that the antisense primers indicated at positions 1268-1287 were used only for DNA sequencing of the product amplified by primer pair A (positions 931-949 and 1462-1439).

Figure 3:
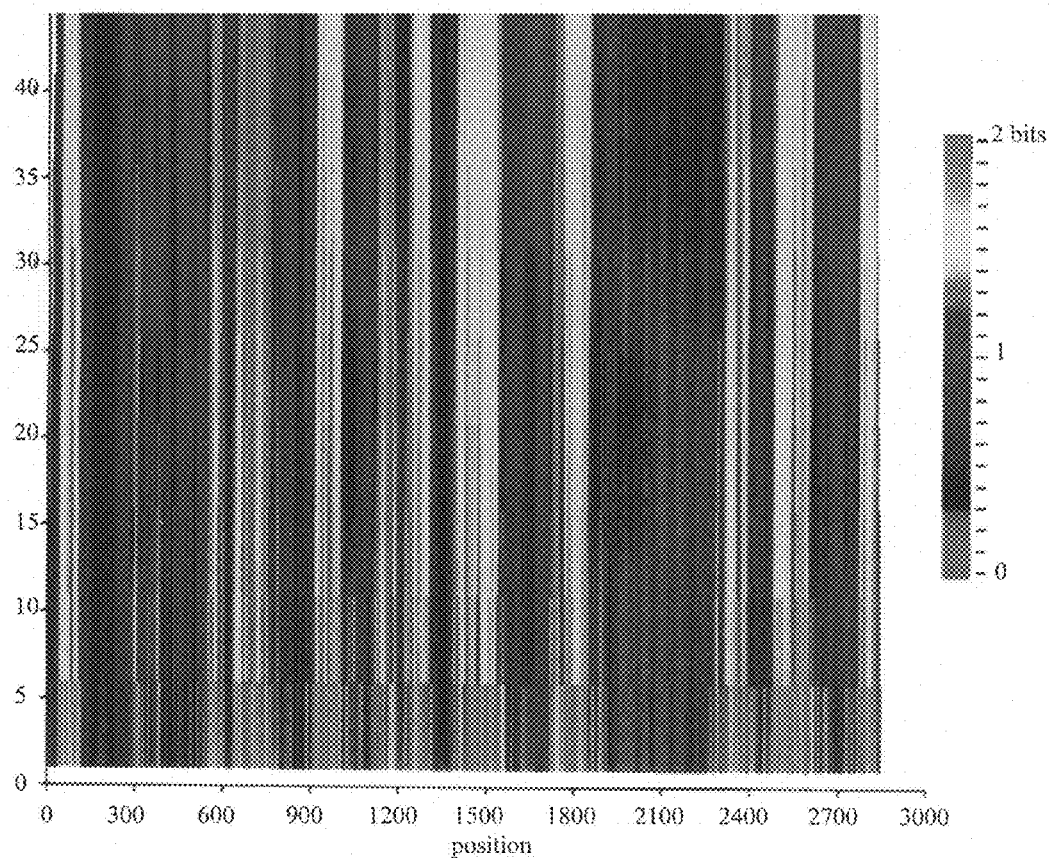
FIG. 3 is a color-coded windowed information plot showing the information content across the entire rDNA gene.

FIG. 3 shows a windowed information plot which indicates the information content across the entire rDNA gene. This figure is color coded by average information content which permits selection of high information content primer length windows separated by a low information content sequence region. Additional sets of primers may be designed in a similar fashion based on the information provided in FIG. 3 as well as sequence logo similar to the logo shown in FIG. 2. Table 1 lists three sets of primers designed based on the methodology described above.

TABLE 1

Degenerate primer sets derived by information analysis

| Primer Set | A | B | C |
|---|---|---|---|
| Forward primer coordinates | 931/949 | 1819/1839 | 1819/1839 |
| Reverse primer coordinates | 1462/1439 | 2391/2370 | 2599/2578 |

PCR products generated from primer set A are approximately 410 nucleotides long, and their DNA sequences may be determined by automated dideoxy methods using internal sequencing primers in less than 1 hour. This procedure simultaneously satisfies the requirements for broad specificity and for high sensitivity and does so rapidly (within a few hours) by comparison with conventional microbiological approaches.

If no amplified bacterial DNA is obtained from a human clinical sample using any of the primers for amplifying bacterial DNA, the sample may be subject to PCR amplification using a pair of test human primers. The test human primers may be a pair of primers that are capable of amplifying a segment of the human DNA. The test human primers preferably anneal to a segment of the human DNA that is highly conserved. If no PCR products are obtained using the test human primers, it is likely that PCR inhibitors may be present in the PCR reaction, because human DNA is abundantly present in the human clinical samples. Conversely, if the expected PCR products are obtained using the test human primers, the bacterial primers may not be suitable for amplifying the unknown species, or there may not be sufficient amount of bacteria in the sample.

If it is determined that PCR inhibitors may be present in the PCR reaction and inhibits DNA amplification, the clinical samples may be diluted. For instance, the 50 ul, and 500 ul centrifugation steps in the standard sample preparation described in Example 1 may be used. If these steps do not solve the problem, it may be necessary to dilute the sample to a higher degree than that used in the standard sample preparation in order to dilute out any possible inhibitors of PCR in the sample. PCR inhibition may be tested by using human ribosomal DNA primers in the PCR reaction as illustrated in Example 1.

Figure 4:
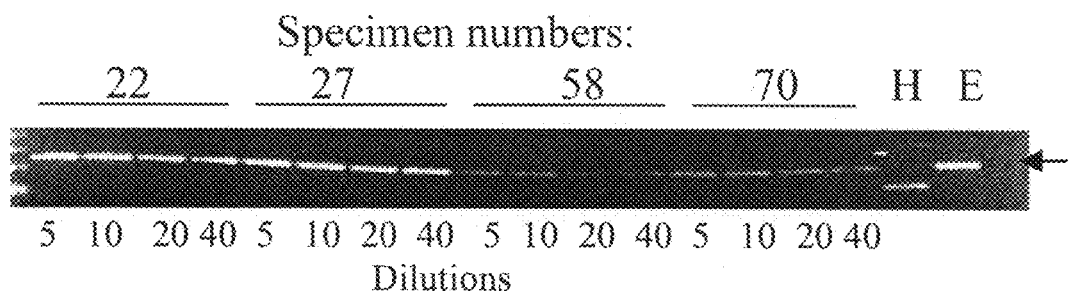
FIG. 4 shows Omnibus PCR analysis of diluted clinical samples containing infectious agents.

FIG. 4 shows Omnibus PCR analysis of diluted clinical samples containing infectious agents. Samples 22, 27 and 58 and 70 were diluted 1:5, 1:10, 1:20 and 1:40 and amplified with primer set A which produces a single PCR product of 415 bp. The human genomic DNA control [H] did not yield a band that comigrated with either *E. coli* (E) or the other bacterial amplification products. Although in this instance all of the dilution produced amplification products, frequently only a subset of dilutions will yield a result.

Figure 5:
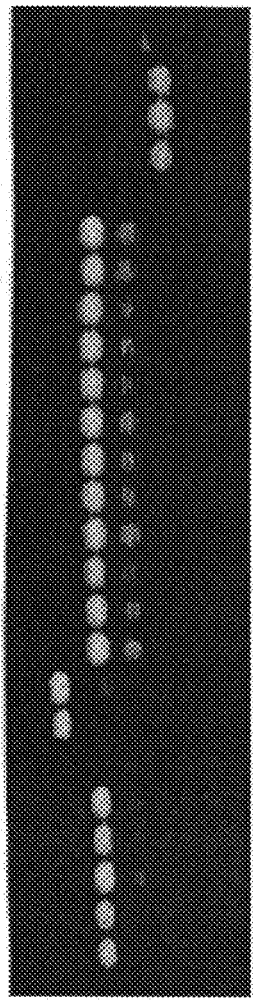
FIG. 5 shows results of Omnibus amplification of a representative sample of 23 different organisms.

FIG. 5 shows results of Omnibus amplification of a representative sample of 23 different organisms. The first 4 organisms were amplified with a different set of omnibus primers from the remaining species (which were amplified using primer set A). Except for *T. globrata* and *C. albicans*, which are fungal agents, most of the bacterial organisms produce the expected 415 bp product.

The PCR product may be purified using a number of established methods for DNA purification. Preferably, the PCR product is purified using magnetic separation, or gel purification. Magnetic separation may have a higher yield of recovered PCR product than gel purification. At least one primer may be biotinylated if magnetic separation of PCR product is to be used. Although gel purification produces relatively lower yield and requires higher amount of the amplified DNA, gel purification has proven helpful in some instances in reducing the problem of concatomers of PCR products that may cause difficulty in obtaining clean sequence data. One potential drawback for gel purification is that it may not be as conducive to automation as magnetic separation. Magnetic separation is the preferred method for purifying the PCR products.

The purified PCR products may be characterized by sequencing or other molecular tools. Sequencing methods such as the dideoxy method or the chemical method may be used. See Sanger F, Nicklen S, Coulson A R, "DNA sequencing with chain-terminating inhibitors." Proc Natl Acad Sci USA. 1977 74(12):5463-7; and Maxam A M and Gilbert W, "Sequencing end-labeled DNA with base-specific chemical cleavages." Methods Enzymol. 1980; 65(1):499-560. The sequences may be read from a film exposed to the sequencing gel or may be obtained using an automated sequencing machine.

Mass spectrometry may also be used to sequence DNA molecules. Briefly, conventional chain-termination reactions may be used to produce DNA molecules of different lengths and the length of these fragments is then differentiated based on the mass differences between them. See e.g., Martin, Genome, 31: 1073, 1989; Nelson et al. Science. 246: 1585, 1989; Jacobsen et al. Genet Anal Tech Appl. December; 8(8): 223-9, 1991; Tang et al. Rapid Communications in Mass Spectrometry, Volume 6, Issue 6, Pages 365-368, 1992; Parr et al. Rapid Communications in Mass Spectrometry, Volume 6, Issue 6, Pages 369-372, 1992; Fitzgerald et al. Rapid Communications in Mass Spectrometry, Volume 7, Issue 10, Pages 895-897, 1993; Wu et al. Anal Chem 66: 1637-1645, 1994; Siuzdak. Proceedings of the National Academy of Sciences, Vol 91, 11290-11297, 1994; Little et al. J. Am. Chem. Soc. 116: 4893-4897, 1994; Tang et al. Nucleic Acids Res. 1995

Aug. 25; 23(16): 3126-3131, 1995; Little and McLafferty. J Am Chem Soc 117, 678306784, 1995; Nordhoff et al. J. Mass Spectrometry, 30(1):99-112, 1995; Barry et al. J. Mass Spectrometry, Volume 30, Issue 7, Pages 993-1006, 1995; Little et al. Proceedings of the National Academy of Sciences, Vol 92, 2318-2322, 1995; Ni et al. Anal. Chem., 68 (13), 1989-1999, 1996; Little et al. J. Am. Chem. Soc., 118 (39), 9352-9359, 1996; Koster et al. Nat. Biotechnol. 1996 September; 14(9): 1123-8; Murray, K. DNA sequencing by mass spectrometry, J. Mass Spectrometry, V. 31, 1203-1215, 1996; J. R. Edwards, H. Ruparel, and J. Ju. "Mass-spectrometry DNA sequencing". Mutation Research 573 (1-2): 3-12 (2005); and U.S. Pat. Nos. 5,691,141, 6,225,450, and 6,268,131. All these references are hereby incorporated by reference into this application.

Other molecular tools capable of discerning the difference in DNA structures may also be used to characterize the PCR products. See, e.g., V. K. Khanna, "Existing and emerging detection technologies for DNA (Deoxyribonucleic Acid) finger printing, sequencing, bio- and analytical chips: A multidisciplinary development unifying molecular biology, chemical and electronics engineering" Biotechnology Advances, 2007, 25:85-98, which is hereby incorporated by reference.

If conventional DNA sequencing is used, when the sequencing run is finished, DNA sequence analysis software, such as Visible Genetics OpenGene, may be used to align and base call the electropherogram. Preferably, the sequence data are manually checked and edited to obtain as clean and accurate a sequence as possible prior to sequence analysis. In some situations, the electropherogram may need to be manually aligned and/or base called because of the limitations of the software.

Figure 6:
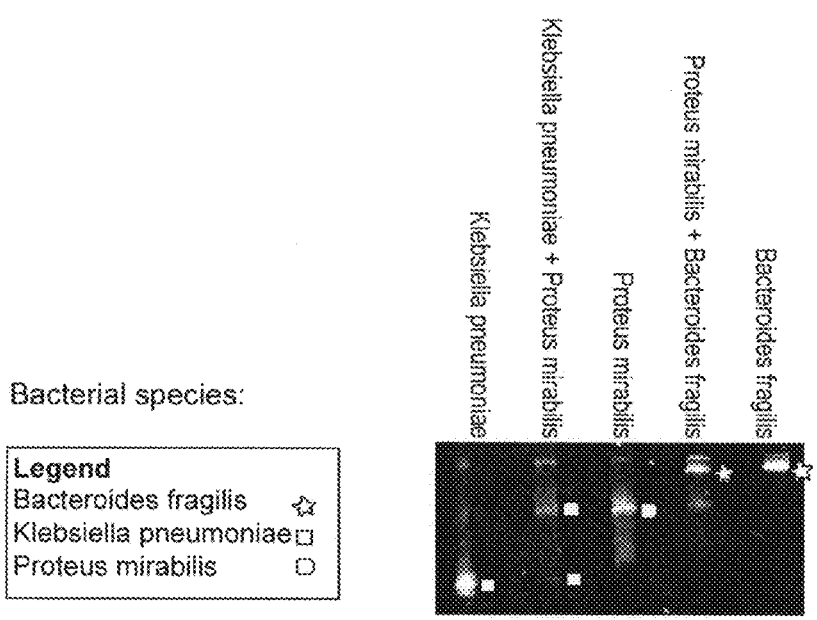
FIG. 6 shows results of separation of PCR amplification products derived from the mixtures of infectious agents by CDGE.

There may be instances where the sequence is not readable because there are multiple peaks at several locations in the sequence. The multiple peaks look a lot like background noise but are usually higher than background noise levels. This phenomenon is called "multiple infection" which refers to the presence of more than one sequences in a sample. One way to determine if there is more than one sequence is to run the sequences on atblast which compares the suspected bacterial sequence with the database of 11,400 prokaryotic 16S rDNA sequences compiled from GenBank using the NCBI Blast software. This method may not work if the sequences can not even be determined in the first place. The sequences derived from most multiple infections will only match approximately 10-30 nucleotides (which is not statistically significant or adequate to determine the identity of the species) due to the resulting limited homology to any single organism rDNA sequence. To solve this problem of deconvoluting the sequences of multiple organisms, a Constant Denaturing Gel Electrophoresis (CDGE) protocol is developed which separates the amplicons produced by each of the species, so that they can be sequenced independently of one another. CDGE may allow DNA to be separated on the basis of sequence in a vertical polyacrylamide gel. FIG. 6 shows a typical CDGE gel which separates the omnibus amplification products from multiple species.

Alternatively, mass spectrometric methods may be employed for simultaneous identification of multiple biomolecular targets. When two or more targets are of similar sequence composition or mass, they may be differentiated by using special mass modifying, molecular weight tags on different targets. These mass modifying tags are typically large molecular weight, non-ionic polymers including but not limited to, polyethylene glycols, polyacrylamides and dextrans. These tags are available in many different sizes and weights, and may be attached at one or more different sites on different nucleic acid molecules. Thus similar nucleic acid targets may be differentially tagged and may now be readily differentiated, in the mass spectrum, from one another by their distinctly different mass to charge ratios. According to this disclosure, the identification process may be significantly accelerated because multiple species may now be identified simultaneously without separating them first.

The following examples illustrate the present invention. These examples are provided for purposes of illustration only and are not intended to be limiting. The chemicals and other ingredients are presented as typical components or reactants, and various modification may be derived in view of the foregoing disclosure within the scope of the invention.

EXAMPLE 1

Clinical Sample Preparation

Materials
  TE buffer
  disinfectant and squirt bottle
  empty container for disinfectant
  0.2 ml strip tubes
  0.2, 0.5, 1.5 ml tubes
  pipettes and sterile pipette tips (1000 ul, 200 ul, 20 ul)
  Red blood cell lysis buffer (if using samples containing blood)
General Strategy
1) Perform standard sample preparation procedure.
2) If this step doesn't result in an amplification product from the sample containing genomic sequences of the pathogen, it is necessary to concentrate the sample by centrifugation of 50 ul or, if available, 500 ul of the sample at high speed (>13000 g). This concentrates the sample containing the template and increases the chance of obtaining an amplification product.
3) If the sample contains red blood cells (whether or not it is a sample of blood), perform sample preparation procedure for blood (#3).
Detailed Protocol
A. Standard Sample Preparation Dilution:
  Put on a disposable lab coat, mask, two sets of gloves and safety glasses
  Label strip tubes with patient number for serial dilution (4 tubes from strip, 1:6, 1:20, 1:50, 1:100)
  To the appropriate labeled tube add the following
    100 ul TE (1:6)
    46 ul TE (1:20)
    30 ul TE (1:50)
    20 ul TE (1:100)
  Cap each tube securely
  Take tubes, samples, tips, pipettes, and disinfectant to a biological safety hood
  Fill disposable box halfway with disinfectant for contaminated tip and tube disposal
  Transfer three 250 ul aliquots of each sample to three labeled 0.5 ml microfuge tubes (to work with)
  Flame the opening of the original clinical specimen tube after opening and before closing
  Place 20 ul of sample into the 1:6 tube and mix thoroughly
    take 20 ul of 1:6 and place into 1:20 tube and mix thoroughly
    take 20 ul of 1:20 and place into 1:50 tube and mix thoroughly
    take 20 ul of 1:50 and place into 1:100 tube and mix thoroughly recap tubes tightly and place used tip into disinfectant Place tubes in thermal cycler and perform Hotstart to kill bacteria 94° C. for 15 minutes 4° C. for infinity Clean and sterilize hood, dispose of all contaminated materials in biological waste container Store remaining clinical sample aliquots and dilutions at −20° C.

Perform PCR amplification on clinical sample dilutions

Typical results for 4 different clinical samples are presented below:

B. Sample Preparation Centrifugation:

Put on disposable lab coat, mask, double gloves and safety glasses.

Fill disposable box halfway with disinfectant for contaminated tip and tube disposal If sample appears bloody, see section labeled sample preparation for samples containing blood Aliquot 50 ul (or 500 ul if 50 ul centrifugation has shown no bacterial amplification) of each sample into a 1.5 ml tube. Make sure tubes are labeled with sample number and other pertinent data.

Centrifuge at 14000 rpm in microcentrifuge for 10 min.

Remove supernatant and discard into disposable box along with pipette tips.

Resuspend pellet with 400 ul TE.

Centrifuge at 14000 rpm in microcentrifuge for 10 min.

Remove and discard supernatant and tips as before.

Resuspend pellet in 50 ul TE, 75 ul TE if using 500 ul centrifugation

Transfer to a labeled 0.2 ml thin walled tube

Place tubes in thermocycler.

Run the "HotStart" program on the thermocycler. This heats the tubes at 94° C. for 15 min. to heat kill the bacteria Clean and sterilize hood, dispose of box containing contaminated materials in biological waste container.

While heat kill program is running, prepare 0.2 ml strip cap tubes for serial dilution as follows:

$1^{st}$ tube straight, $2^{nd}$ tube 1:6, $3^{rd}$ tube 1:20 and $4^{th}$ tube 1:50

Place 100 ul TE into tube 2

Place 46 ul TE into tube 3

Place 30 ul TE into tube 4

When hotstart program is finished, place 20 ul sample into straight tube and 20 ul sample into $2^{nd}$ tube labeled 1:6 and mix thoroughly Take 20 ul from 1:6, place into 1:20 tube and mix thoroughly Take 20 ul from 1:20 tube, place into 1:50 tube and mix thoroughly Store remaining clinical sample aliquots and dilutions at −20° C.

Perform PCR amplification on sample dilutions

C. Sample Preparation for Samples Containing Blood*

Put on disposable lab coat, mask, double gloves and safety glasses.

Fill disposable box halfway with disinfectant for contaminated tip and tube disposal Add 300 ul red blood cell lysis buffer to a labeled 1.5 ml microfuge tube In a biological safety hood—add 100 ul sample to tube and mix Incubate 10 minutes with periodic mixing Centrifuge 11700 rpm (14500×g) for 1 min.

Save pellet and discard of supernatant

Wash pellet with 300 ul red blood cell lysis buffer

Centrifuge 11700 rpm (14500×g) for 1 min.

Save pellet and discard of supernatant

Resuspend pellet in 50 ul TE

Transfer to a labeled 0.2 ml thin walled tube

Cap tightly and place in thermalcycler, run HOTSTART (94° C. for 15 min.) to heat kill bacteria Clean and sterilize hood, dispose of contaminated material in biological waste container Set up sample dilutions the same as described under the section labeled "Sample Preparation Centrifugation"

Store remaining clinical sample aliquots and dilutions at −20° C.

Perform PCR amplification on clinical sample dilutions

*Heme is an inhibitor of PCR

D. Preparation of Infected Solid Tissue Specimens for Bacterial DNA Amplification 1) Add PBS to thawed sample
2) Let stand for 15 minutes Alternative: If no amplification is obtained, rock on nutating platform 3-4 hours, then continue with step 3.

3) Remove PBS, centrifuge
4) Remove supernatant and wash pellet with TE
5) Centrifuge, resuspend in TE
6) Perform sample dilutions as in centrifugation sample prep.
7) If this does not work, grind tissue first with tissue grinder.

EXAMPLE 2

Preparation of Sequence Logo

A sequence logo was created from the aligned 16S rDNA sequences, and a representative region having two conserved regions surrounding a divergent region is shown in FIG. 2. The horizontal axis represents nucleotide positions along the DNA, whereas the vertical axis measures the degree of conservation at the same position in the various species. The vertical scale is given in bits of information (or $R_{sequence}$), which measures the number of choices between two equally likely possibilities. $R_{sequence}$ may be calculated according to Equation I.

The choice of one base from the 4 possible bases requires two bits of information. The two bits correspond to two choices. For example, the first choice could determine whether the base is a purine or a pyrimidine and the second choice would specify which purine or pyrimidine is present. Thus, if at a certain position, all of the aligned 16S sequences have the same nucleotide, then that position has two bits of conservation. Thus, in the logo of FIG. 2, that nucleotide appears at that particular position with a height of (almost) 2 bits. A small sample correction prevents it from being exactly 2 bits high (Schneider T. D. et al., 1986, J. Mol. Biol., 188: 415-431).

For those positions where two equally likely bases occur, there is only one bit of information. This is because a choice of 2 things from 4 is equivalent to a choice of 1 thing from 2. By way of example, if at a particular position in a nine-sequence alignment, 5 of the sequences contain A and 4 have T, this position is about 1 bit high in FIG. 2. The relative frequency of the bases determines the relative heights of the letters, and since A is more frequent, it is placed on top. A position in which all four bases are equally likely is not conserved and so has an $R_{sequence}$ of zero and its height on the logo is zero. When the frequencies of the bases are other than 0, 50 or 100 percent, the heights still measure the conservation at each position, and the calculation may be performed according to Equation 1.

EXAMPLE 3

Design of Primers

In order to perform a PCR, two segments of DNA (which are referred to as primers) may be designed and prepared. The two PCR primers represent a set of oligomers in which set the frequency of a nucleotide is proportional to its presence at this particular position in the sequence logo prepared based on a number of 16S rDNA sequences from different organisms. The primers were designed according to the following three criteria: (1) They are in regions of high conservation, and surround regions of low conservation. (2) The 3' termini cover regions that are invariant between species, so that the primer end which is extended by the DNA polymerase is always properly annealed to the DNA. (3) The oligonucleotide primers are not self complementary and do not base pair to each other. The primers may also contain restriction sites useful for subsequent cloning of the amplification product.

The following primers have been designed based on the Logo prepared in Example 2, and the relative positions of Primer Set A is shown in FIG. 2:

Primer Set A:

Forward:
(SEQ ID. NO. 1)
5'- G T G($C_{0.988}$/$G_{0.006}$/$T_{0.006}$) CAGC ($A_{0.95}$/$C_{0.038}$/

$G_{0.006}$/$T_{0.006}$) G ($C_{0.994}$/$T_{0.006}$) ($A_{0.006}$/$C_{0.982}$/

$G_{0.006}$/$T_{0.006}$) ($C_{0.006}$/$G_{0.988}$/$T_{0.006}$) ($C_{0.994}$/

$T_{0.006}$) G G T -3'

Reverse:
(SEQ ID. NO. 2)
5'- C C($C_{0.994}$/$A_{0.006}$) ($T_{0.006}$/$G_{0.988}$/$A_{0.006}$)

($T_{0.939}$/$C_{0.055}$/$A_{0.006}$) C ($T_{0.041}$/$A_{0.959}$) A T ($T_{0.988}$/

$C_{0.006}$/$A_{0.006}$) ($T_{0.033}$/$C_{0.961}$/$A_{0.006}$) ($T_{0.006}$/

$G_{0.006}$/$C_{0.853}$/$A_{0.135}$) ($T_{0.994}$/$C_{0.006}$) T ($T_{0.994}$/

$G_{0.006}$) ($G_{0.922}$/$A_{0.072}$/$C_{0.006}$) ($A_{0.994}$/$G_{0.006}$)

($G_{0.994}$/$C_{0.006}$) T ($T_{0.994}$/$A_{0.006}$) ($T_{0.994}$/$G_{0.006}$) -3' wherein the subscripts represent the relative abundance of the corresponding nucleotide at that position in the sequence as determined by information analysis of a large number of multiply-aligned sequences from a wide variety of prokaryotic species.

Primer Set B:

Forward:
(SEQ ID. NO. 3)
5'- ($G_{0.954}$/$T_{0.043}$/$A_{0.002}$/$C_{0.001}$) ($G_{0.978}$/$C_{0.02}$/

$T_{0.002}$) ($T_{0.9985}$/$G_{0.0015}$) ($T_{0.992}$/$C_{0.006}$/$A_{0.002}$)

($A_{0.989}$/$C_{0.004}$/$T_{0.007}$) ($A_{0.998}$/$T_{0.002}$) ($G_{0.998}$/

$A_{0.002}$) ($G_{0.003}$/$C_{0.001}$/$T_{0.996}$) ($C_{0.975}$/$G_{0.021}$/

$T_{0.004}$) ($C_{0.952}$/$A_{0.042}$/$T_{0.005}$/$C_{0.001}$) ($A_{0.009}$/$C_{0.882}$/

$G_{0.063}$/$T_{0.046}$) ($A_{0.052}$/$C_{0.002}$/$G_{0.943}$/$T_{0.003}$)

($A_{0.005}$/$C_{0.890}$/$G_{0.003}$/$T_{0.102}$) A A C G A -3'

Reverse:
(SEQ ID. NO.4)
5'- C A($T_{0.996}$/$C_{0.002}$/$A_{0.002}$) ($T_{0.996}$/$G_{0.002}$/

$A_{0.002}$) G ($C_{0.005}$/$T_{0.995}$) A ($T_{0.062}$/$G_{0.914}$/$A_{0.024}$)

($T_{0.074}$/$G_{0.039}$/$C_{0.887}$) ($T_{0.004}$/$G_{0.008}$/$C_{0.043}$/

$A_{0.945}$) ($T_{0.097}$/$C_{0.903}$) G ($T_{0.911}$/$C_{0.088}$/$A_{0.001}$)

($G_{0.982}$/$T_{0.018}$) T ($G_{0.998}$/$C_{0.002}$) ($T_{0.834}$/$C_{0.036}$/

$A_{0.130}$) ($A_{0.032}$/$C_{0.029}$/$G_{0.057}$/$T_{0.882}$) C C C -3' wherein the subscripts represent the relative abundance of the corresponding nucleotide at that position in the sequence as determined by information analysis of a large number of multiply-aligned sequences from a wide variety of prokaryotic species.

Primer Set C:

Forward:
(SEQ ID. NO. 5)
5'- ($G_{0.954}$/$T_{0.043}$/$A_{0.002}$/$C_{0.001}$) ($G_{0.978}$/$C_{0.02}$/

$T_{0.002}$) ($T_{0.9985}$/$G_{0.0015}$) ($T_{0.992}$/$C_{0.006}$/$A_{0.002}$)

($A_{0.989}$/$C_{0.004}$/$T_{0.007}$) ($A_{0.998}$/$T_{0.002}$) ($G_{0.998}$/

$A_{0.002}$) ($G_{0.003}$/$C_{0.001}$/$T_{0.996}$) ($C_{0.975}$/$G_{0.021}$/

$T_{0.004}$) ($C_{0.952}$/$A_{0.042}$/$T_{0.005}$/$G_{0.001}$) ($A_{0.009}$/

$C_{0.882}$/$G_{0.063}$/$T_{0.046}$) ($A_{0.052}$/$C_{0.002}$/$G_{0.943}$/$T_{0.003}$)

($A_{0.005}$/$C_{0.890}$/$G_{0.003}$/$T_{0.102}$) A A C G A - 3'

Reverse:
(SEQ ID. NO. 6)
5'- ($T_{0.996}$/$A_{0.002}$/$G_{0.002}$) ($C_{0.994}$/$G_{0.001}$/$T_{0.005}$)

($T_{0.993}$/$C_{0.005}$/$G_{0.002}$) ($G_{0.995}$/$C_{0.001}$/$A_{0.004}$)

($A_{0.996}$/$T_{0.0025}$/$C_{0.0015}$) ($C_{0.997}$/$A_{0.0015}$/$G_{0.0015}$) G ($G_{0.998}$/$A_{0.002}$) ($G_{0.996}$/$C_{0.004}$) ($C_{0.998}$/$G_{0.002}$)

($G_{0.971}$/$A_{0.027}$/$C_{0.002}$) G T ($G_{0.999}$/$T_{0.001}$) ($T_{0.953}$/

$A_{0.047}$) G T ($A_{0.946}$/$G_{0.054}$.) C A -3' wherein the subscripts represent the relative abundance of the corresponding nucleotide at that position in the sequence as determined by information analysis of a large number of multiply-aligned sequences from a wide variety of prokaryotic species.

Primer sets A, B or C may be used separately to amplify the 16S rDNA sequences of a prokaryotic organism.

EXAMPLE 4

PCR Reactions

Materials
PCR reagents—see table below
Clinical sample dilutions, or purified samples (−20° C.)
Purified *E. coli* and human DNA (100 ng/μl)
1.5 or 2.0 ml centrifuge tubes
0.2 ml strip tubes or thin-wall thermocycler plates
pipettes and sterile pipette tips (1000 μl, 200 μl, 20 μl, 10 μl)

Preparation of Reaction Components
Obtain reagents from the freezer and place on ice. (ensure that all reagents are completely thawed and well mixed prior to use)

Calculate amount of each reagent needed based on following table [use number of sample dilutions and controls to be amplified+2 (for pipette error)]
Mix PCR cocktail in 1.5 or 2.0 ml sterile centrifuge tube.

TABLE 2

Cocktail for Preparation of the PCR Reaction

| PCR Cocktail | μl/reaction | Final Concentration |
|---|---|---|
| RNase-free, DNase-free Water Room temp. | 30.58 | na |
| 1.25 mM dNTP −20° C. | 7.9 | 200 μM |
| 25 mM MgCl$_2$ −20° C. | 4 | 2.0 mM |
| 10 × PCR Buffer (Mg free) −20° C. | 5 | 1 X |
| 50 μM primer 931949* (forward) −20° C. | 0.6 | 0.6 μM |
| 50 μM primer 14621439* (reverse) −20° C. | 0.6 | 0.6 μM |
| 100% formamide 4° C. | 0.875 | 1.75% |
| 20 mg/ml BSA −20° C. | 0.245 | 0.098 mg/ml |
| 5 U/ul Taq Polymerase** −20° C. | 0.2 | 1 U/50 ul reaction |

*one primer may be biotinylated if magnetic separation of PCR product is going to be used, this labeled primer is preferably diluted 1:5 (1 part primer, 4 parts water).
**Taq Polymerase should be kept at −20° C. until just before PCR is performed (add last)

With each PCR amplification reaction, run two positive controls and one negative control:
  Positive Controls:
    50 μl PCR cocktail, 2 μl control DNA (stored at −20° C., 100 ng/μl)
    prepare 1 *E. coli* DNA and 1 human genomic DNA
  Negative Control:
    50 μl PCR cocktail
  Add 50 μl of PCR cocktail to 0.2 ml PCR strip tubes or plate at 4° C. (one for each sample dilution and control)
  Add 2.5 μl of clinical sample (see sample prep) or 2.0 μl of purified sample (controls or purified DNA samples)
  Run Omnipcr program on MJ Alpha thermocycler

| OmniPCR program (2 hr. 20 min.) | | |
|---|---|---|
| Cycle | Temperature | Time |
| 1 | 95° C. | 2 min. |
| 2 | 95° C. | 30 sec. |
| 3 | 50° C. | 45 sec. |
| 4 | 72° C. | 45 sec. |
| 5 | 35 times to cycle 2 → 3 → 4 | |
| 6 | 72° C. | 10 min. |
| 7 | 4° C. | hold |

Store at 4° C. after PCR is complete.
Run results on a 2% LE agarose gel to determine which samples amplified bacterial DNA (see agarose gel procedure)

EXAMPLE 5

Agarose Gel Detection of PCR Products

Materials:
10-15 μl PCR product
3× loading buffer
123 bp ladder (optional)
Fisher, Molecular Biology Grade Agarose
Gel box and combs
P20 pipette and tips
Ethidium Bromide
Microwave oven
0.5×TBE buffer
Erlenmeyer flask for making gel
Graduated cylinder
Detailed Protocols:
  Prepare gel box for pouring gel
  Prepare a 2% agarose gel (add 2 grams/100 ml agarose to 0.5×TBE)
  Microwave on high power for 2 min. Stop every 10-15 seconds and swirl until all agarose has dissolved.
  Allow to cool slowly by placing at 55° C. for 10 minutes
  Add 3 μl 1% Ethidium Bromide solution and carefully swirl to mix in EtBr (do not swirl too vigorously or air bubbles will be produced). EtBr is a CARCINOGEN—WEAR GLOVES.
  Pour gel into tray, place comb in appropriate position and allow gel to solidify
  Remove rubber end pieces carefully. Fill gel box with 0.5×TBE until gel is just submerged. Carefully remove comb while submerged.
  Cut off a piece of parafilm and pipette 3 ul of 3× loading buffer onto the parafilm for each sample and ladder.
  Add 3 ul of ladder solutions (optional) to loading buffer (one on each end). Add 10-15 ul of 0.5×TBE buffer to these.
  Add 10-15 ul of 0.5×TBE to ladder solutions
  Add 10-15 ul PCR product to remaining loading buffer.
  Load samples onto gel and run between 100-125 V for 30-45 min. at room temperature.
  Place gel on UV light box to visualize.
  Photograph gel for documentation.
  Bacterial bands can be visualized by corresponding band location on the samples to that of the *E. coli* control and DNA ladder.
  Be sure to note any contamination in the negative control which may also indicate contamination in the other samples.
Typical results of the PCR amplification reaction for a wide variety of infectious agents are shown in FIG. 5.

EXAMPLE 6

Cycle Sequencing of the PCR Products

Materials
  Magnetically separated PCR products or Gel purified PCR product
  Visible Genetics 7-deaza* Thermosequenase cycle sequencing kit (Cat# US79608):
    A, C, G, T termination mixes (7-deaza G)
    Thermo Sequenase enzyme
    Enzyme dilution buffer
    Sequencing Buffer I
    Cy5.5 or Cy5.0 labeled sequencing primer (3 μM)
    0.2 mL thin walled tubes (4 tubes per sample)
*7-deaza G termination mixes reduce the formation of secondary structures in the target DNA which cause poor sequencing results.
Preparation of Reaction Components
  Remove all reagents from freezer and thaw on ice. Mix well before use.

Label four tubes for each PCR product: A, C, G, T. Aliquot 3 μL of each of the A, C, G, and T termination mixes into their labeled tubes respectively at 4° C.

Make an aliquot of 1:10 diluted Thermo Sequenase enzyme (9 parts enzyme dilution buffer: 1 part Thermo Sequenase enzyme). Place on ice.

Add the following to 14 μl of the magnetically separated or gel purified PCR products:
2.5 μl Sequencing Buffer I
2.5 μl Cy5.5 of Cy5.0 labeled nested primer (3 μM)
3.0 μl diluted (1:10) Thermo Sequenase enzyme mix well Aliquot 5 μl of the above mix into each of the termination tubes. Mix well by pipetting up and down.

Place tubes in thermocycler and run cycle sequencing program (CYCLMOD2 or CYCLE2 on PTC-200)

One Step Cycle Sequencing:

| CYCLEMOD2 program: (1 hr. 30 min.) | | | |
|---|---|---|---|
| Stage | Temp. | Time | #cycles |
| 1) Denaturation | 94° C. | 2 min | 1 |
| 2) Cycle | 94° C. | 40 sec | 25* |
|  | 50° C. | 20 sec |  |
|  | 72° C. | 60 sec |  |
| 3) Final extension | 72° C. | 2 min | 1 |
| 4) Soaking | 4° C. | infinity |  |

*At Step 2, during each cycle, the samples are subject to three different temperatures sequentially for the indicated time period, and this 3-step cycle is repeated 25 times.

Two Step Cycle Sequencing: (May Help Reduce Hard Stops Due to Secondary Structures)

| CYCLE2 program: (1 hr. 30 min.) | | | |
|---|---|---|---|
| Stage | Temp. | Time | #cycles |
| 1) Denaturation | 94° C. | 2 min | 1 |
| 2) Denaturation | 94° C. | 20 sec | 20* |
| Annealing | 50° C. | 20 sec |  |
| Extension | 72° C. | 60 sec |  |
| 3) Denaturation | 94° C. | 20 sec | 20** |
| Extension | 72° C. | 60 sec |  |
| 4) Final extension | 72° C. | 2 min | 1 |
| 5) Soaking | 4° C. | −infinity |  |

*At Step 2, during each cycle, the samples are subject to three different temperatures sequentially for the indicated time period, and this 3-step cycle is repeated 20 times.
**At Step 3, during each cycle, the samples are subject to two different temperatures sequentially for the indicated time period, and this 2-step cycle is repeated 20 times.

Samples are now ready for automated DNA sequencing.

EXAMPLE 7

CGDE to Identify Multiple Organisms in the Same Sample

The percent denaturant can be varied to maximize the separation of the DNA on the gel. Currently gels containing 30% denaturant are run. Using the temperature controlled, Owl vertical gel electrophoresis unit (Owl Scientific), 75-80 ml of appropriate percentage gel to cast one CGDE. For this example 30% denaturant will be used. Mix 52.5 ml of 0% denaturant, 22.5 ml of 100% denaturant and 323 μl of 20% APS in a vacuum flask. Remove the air by placing under vacuum for several minutes. After the air is removed add 138 μl of TEMED. Swirl gently and add the gel mixture to the glass plates.

Preparation of the Gel Apparatus and Peristaltic Heating Unit:

The circulating heater bath to control gel box temperature must be turned on- and running through the gel box at 60 C. The plates used for CDGE need to be cleaned with soap and water and also with 95-100% ethanol. Plastic spacers are placed between the plates to separate multiple gels. The plates are then placed inside a plastic freezer bag. Cut the top of the freezer bag off so it is approximately the same height as the glass plates, this allows for easier pouring of the gel. Once this is done place the bag/plate sandwich in the Joey gel casting system (Owl Scientific) and tighten the screws down. Place the comb between the plates making sure that the wells are only about 5 mm below the top of the glass plates. If the wells are too deep, the samples will disperse during loading, resulting in pour resolution. This setup should be performed before the acrylamide is degassed prior to pouring the gels.

Casting the Gel:

Once the gel casting system is assembled and the gel is ready to pour you will need to get a 1000 μl pipet tip and the 60 CC syringe. Cut about 3 mm off the end of the pipet tip with a scalpel and attach to the syringe. Pour the gel from the vacuum flask into an appropriately sized beaker (so you can fit the syringe into the gel). Suck up the gel with the syringe and add between the glass plates. The space between the plates filling with the gel should be visible. Fill the plates to the top with the gel. Once the gel is poured, wait 15-30 min. until it has polymerized.

Final Gel Preparation:

After the gel has polymerized remove it from the gel casting system and the plastic bag. Scrape any excess polyacrylamide from the outside of the plates. Wiping the plates with a damp paper towel after scraping the excess off helps remove any residual polyacrylamide. Place the plate/gel sandwich in the vertical gel box that has the 60 degree water running through it (you should have turned the heater for the water on earlier-make sure to check the volume of water in the heater). Place 1×TBE buffer in the bottom of the gel box and between the gel and the vertical part of the box. Unless two gels are being run, the other side of the gel box should have a plastic plate in it so the buffer can fill the vertical part of the chamber and cover the platinum wire that generates the current. Remove the comb and straighten the polyacrylamide between the gels for easier loading. The gel can now be loaded.

Sample Preparation, Loading and Electrophoresis:

The samples used for CDGE should come from 100 ul PCR reactions so there is enough DNA to detect by CDGE. Make sure to do an agarose gel check to verify that sufficient amplification product is available before running the sample on a CDGE. If there is ample DNA add 20-25 μl of CDGE loading dye (contains 50% formamide) to the sample, place in thermocycler and run CDGE3 program. Once the program is finished, add ~20 μl of sample to the wells and run the gel. The gel is run at 60 mA for 4-4.5 hours. Once the gel is done running remove it from the gel box and remove one of the glass plates. Make sure you mark the gel so you know the orientation. Remove the plastic spacers and plate the plate with the gel inside a plastic bag and in one of the gel dying trays.

Staining the Gel and Photographic Exposure:

Once the gel is in the bag in the dying tray add 300 ml of dye (Gelstar SYBER Green-2×). Placing the gel in the bag allows more of the dye to get on the gel (you can fold the bag up to move more dye onto the gel). Cover the gel/gel tray with aluminum foil and stain gel for 30 minutes. After the gel is stained, remove it from the bag and place on seran wrap (the stain can be dumped from the bag and saved-dye is good for several days if kept in fridge and covered). Use the seran wrap to cover the gel and flip it so the gel can be removed from the glass plate. Once the plate is removed place the gel on the UV-light box and look at it. Photograph the gel with the electronic digital camera and cut out bands and elute the DNA for DNA sequencing.

EXAMPLE 8

Obtaining and Editing Sequencing Results

Editing an Automatically Aligned and Base Called Electropherogram:

Click on the sample to be edited to bring up the curve viewer of sequence data for that sample. Smaller regions of the electropherogram can be viewed and edited by shortening and moving the zoombox above the sequence data.

First view the signal strength of the region between the primer peak and the end of sequence peak (this is the region of our target DNA sequence). The peak heights should be at least 1,000 as indicated on the left of the sequence under the viewing options. If signal strength is too weak, clean sequence data cannot be achieved. Also, if the peak heights of the sequence data are too high (above the threshold of the software), the peaks will flatten on the top and clean sequence data cannot be achieved. Optimal peak height is approx. 1,000 to 4,000, however, it may be possible to achieve clean sequence outside this range.

If the electropherogram has been automatically aligned and base called, check the run overview. The less black and grey sections on the bottom portion of the run overview, the better the sequence quality.

Scroll through the sequence to visually check the accuracy of the automated alignment and base calling. If the electropherogram appears to be aligned and base called accurately, continue with the procedure below. If not, the electropherogram may need to be manually aligned and/or base called (see section below "Manually aligning and base calling and electropherogram").

OPTION: Under TOOLS, BASE CALLING, ATTRIBUTES, the heterozygote stringency can be changed to achieve more accurate sequence results. PURE (~50%) has proven to work well in the past. If you change the heterozygotes function, re-base call the sequence by selecting BASECALL under MANUAL and click on GO.

Start from the primer peak region and scroll through slowly. Make any adjustments to the electropherogram that are necessary (the software will occasionally miscall bases). Add a base by clicking on the location the base belongs and typing the appropriate letter. Delete a base or bases by highlighting the region containing the base/bases to be deleted and pressing the backspace button. If a region of the electropherogram is unclear as to what the sequence should be, insert an appropriate amount of n's in this region.

Make sure to delete the bases called, if any, in the primer peak region, end of sequence peak region, and any other region of the electropherogram not containing the target DNA sequence. It may also be necessary to delete up to the first 20 bases past the primer peak and before the end of sequence peak if these regions of the electropherogram are poorly aligned and/or base called. Try to keep as much sequence data as possible while maintaining a high degree of accuracy.

Save the electropherogram. This file is now ready for sequence analysis.

Manually Aligning and Base Calling an Electropherogram:

If the electropherogram is aligned well but not base called, manually base call the electropherogram by clicking on each peak and typing the appropriate base. Insert Ns where the sequence is unclear.

If the electropherogram is poorly aligned:

1) Check the quality of sequence data by scrolling through the electropherogram. The tiled function under the viewing options in the curve viewer can be selected to view each lane separately. If the background noise is high or if the peaks on the electropherogram are not clear and distinct from each other, then clean sequence data cannot be achieved from this electropherogram. If the peaks for each lane appear clean and distinct from each other with low background noise, then continue to step 2 below.

2) You can try adjusting the peak distance (under TOOLS, BASE CALLING, ATTRIBUTES). The software attempts to automatically align the electropherogram at a default setting of 8.00 for peak distance. The actual peak distance will be most likely be somewhere between 5 and 8. You can attempt to adjust the peak distance and select ALIGN, under MANUAL and click on GO to re-align the electropherogram. By trial and error, this may produce an accurate alignment. If not, continue to step 3 below.

3) Manually align the sequence:
    Under MANUAL, click on RESET TO RAW
    Start at end of sequence peak. Under ALIGN POINTS, ADD and align point to the end of sequence peak. Click on SHOW under ALIGN POINTS. Click on the align point you just added.
    Adjust the four lanes using the arrows under manual alignment until the end of sequence peak is aligned in all four lanes.
    Add another align point about 20 nucleotides before the end of sequence peak, click on it.
    Adjust the four lanes (in the same manner as before) until they are aligned between the two align points.
    Add another align point about 20 nucleotides before the last one and align the lanes as above. Continue this until the entire sequence is aligned.

Manual alignment takes practice and requires trial and error. A user may need to start at a different place in the electropherogram or use different methods from those listed above. Even if peaks for each lane on the electropherogram appear clean and distinct with low background noise, alignment may be impossible due to a multiple infection creating peaks in more than one lane in the same location.

If alignment of the electropherogram is achieved, the electropherogram may or may not be able to be automatically base called. To attempt automatic base calling, select BASECALL under MANUAL and click on GO.

If the sequence doesn't base call, manually base call by clicking on each peak and typing the appropriate letter.

If a sequence is achieved, save the electropherogram. This file is now ready for sequence analysis.

EXAMPLE 9

Sequence Analysis

After a "clean" assay sequence is achieved, it is then assembled into a contig by comparison with other "clean" overlapping and complementary sequences from the same specimen, and the consensus sequence is derived from the contig sequence. The sequence analysis containing this sequence is performed to identify the organism based on the rDNA sequence. The consensus sequence (or the assay sequence) is then compared to a database of approx. 11,400 prokaryotic 16S rDNA sequences. A quick sequence analysis can be performed by running atblast (a software script which compares the test sequence with this database using the NCBI Blast engine) on the Sun 5 scientific workstation. Atblast will display the best 50 matches and pairwise alignments from a blast search comparing our sequence with the sequence database. An, in depth, comprehensive analysis can be performed by running atblasttest on the Sun workstation. This program will perform a Blast search as in atblast, followed by a multiple sequence analysis to relates the consensus or assay sequences to the most closely related organisms demonstrated by the Blast search, and then computes and displays two different types of phylogenetic trees based on the relationships between these closely related, multiply-aligned sequences (Parsimony and Neighbor-joining trees). Atblasttest will save all of the relevant files for each analysis under a time-date stamped folder for each assay or consensus sequence file entered.

Running the atblast script
  On the Sun workstation, open a terminal window and enter atblast at the prompt.
  On the Visible Genetics' computer, make sure ShiptoSun folder (Users>Lab>Data>LAB>ShiptoSun) contains no assay files. The ShiptoSun script looks at this folder and exports the results of the sequence analysis to the Sun workstation where the atblast analysis commences. If it does, move these files back to the appropriate folders.
  Place the assay file containing the sequence to be analyzed in the ShiptoSun folder.
  Open the terminal shell on the Visible Genetics computer.
  At the visgen1>prompt, type ftpSun
  Within 20 seconds, the output from the atblast file will be displayed on the Sun workstation.
  Compare the atblast results with the electropherogram for the assay file you just sent to the Sun workstation. Look for differences between the reference sequence and your sequence in the atblast output. Check the locations of these differences on the electropherogram on the Visible Genetics computer and make any changes that are necessary. NOTE: Only make changes on the electropherogram in locations where the sequence is clearly incorrect.
  If changes are made to the assay file based on the atblast results, save the assay file. NOTE: The assay file will be saved in its original location and not in the ShiptoSun folder, so if the updated assay file is to be sent back to the Sun workstation for further analysis, it must be put into the ShiptoSun folder from its original location.
  Record any pertinent information from the atblast file (species of closely matching sequences, # nucleotides, % match, etc.)
  Atblast analysis may be sufficient for some applications. If the assay file being sent contains a new clinical specimen sequence, atblasttest should be performed for a complete sequence analysis.
Running the Atblasttest Script:
  Set up atblasttest exactly as atblast above (except for the different program name entered into the Sun workstation)
  Output for atblasttest takes approx. 30 min.
  After atblasttest is finished running, five windows will be displayed:
    1) The terminal window—describing the program's processes that were performed
    2) Primary sequence analysis report—basic blast search
    3) Clustal X— a color coded multiple sequence analysis
    4) Treetool: newseqtree.ph—a phylogenetic tree analysis
    5) newseqtree.ph—a different phylogenetic tree analysis
  Compare the multiple sequence alignment to your original electropherogram. Look for positions where differences occur in the sequences shown in the multiple sequence alignment. Compare these positions to you sample's sequence and electropherogram. Make any changes to your sample's electropherogram that seem apparent. If any changes are made, perform atblasttest again.
  Observe the phylogenetic tree files to see the phylogenetic relationship between your sample sequence and closely related sample sequences. The two tree files created may show a different phylogenetic relationship because of different tree forming algorithms used in each.
  To close and save the windows generated by atblasttest (must be done before another atblasttest analysis is performed):
    1) Under the ClustalX window, write the alignment as postscript (under FILE), then quit (under FILE). A postscript multiple sequence analysis will then be shown, this can be printed or closed.
    2) Under the Treetool: newseqtree.ph window, under FILE with the right mouse button, select quit.
    3) Under the newseqtree.ph window, click on SAVE TREE, then close.
    4) Under the Preliminary Sequence Analysis Report, close window.
  The terminal window will indicate the filename under which the atblasttest files for that sample sequence are located.

EXAMPLE 10

Feasibility Study

In order to determine whether the primers and the methods of the present disclosure work across a broad spectrum of species, purified organisms were obtained and cultured in a laboratory setting. Genomic DNAs were extracted from these cultured organisms and used as template for PCR using Primer sets A, B and C. The results of the PCR reactions are summarized in Tables 3 and 4. The PCR products shown in Table 4 were also subject to sequencing using primer A which results are shown in the same Table.

TABLE 3

Feasibility Test Using Purified Organisms

| | 931/949 1462/1439 | 1819/1839 2391/2370 | 1819/1839 2599/2578 |
|---|---|---|---|
| Acinetobacter | + | + | + |
| Actinobacillus | + | + | + |
| Actinomyces pyogenes | + | + | + |
| Actinomyces pyogenes | + | + | + |
| Aeromonas hydophilia | + | + | |
| Alcaligenes fecalis | + | | + |
| Aligella urethralis | + | + | + |

TABLE 3-continued

Feasibility Test Using Purified Organisms

| | 931/949 1462/1439 | 1819/1839 2391/2370 | 1819/1839 2599/2578 |
|---|---|---|---|
| *Alteromonas putriaciens* | + | + | + |
| *Alteromonas putrifuciens* | + | + | + |
| *Bacteriodes distasonis* | + | | |
| *Bacteriodes fragila* | + | | |
| *Bacteriodes melaninogenicum* | + | + | + |
| *Bacteriodes ovatus* | + | + | + |
| *Bacteriodes thetaiomicion* | + | + | + |
| *Bacteriodes uniformis* | + | + | + |
| *Campylobacter* | + | + | |
| *Candida albicans* | + | | |
| *Capnocytophaga* | + | nd | nd |
| CDC group IVc | + | nd | nd |
| *Chlamydia trachomatis* | + | | |
| *Citrobacter fruendii* | + | + | + |
| *Clostridium difficle* | + | + | + |
| *Clostridium histolyticum* | + | + | + |
| *Clostridium perfingens* | + | + | + |
| *Clostridium septicum* | + | + | + |
| *Clostridium sordelli* | + | + | + |
| *Clostridium sporogenes* | + | + | + |
| *Corynebacterium diptheria* | + | | |
| *Corynebacterium pseudodoi.* | + | | |
| *E. coli* | + | + | + |
| *E. coli* 0157-H7 | + | nd | nd |
| *E. coli*-β lactamase positive | + | nd | nd |
| *Enterobacter aerogenes* | + | + | + |
| *Enterobacter cloecae* | + | + | + |
| *Enterobacter fecalis* | + | | |
| *Eubacterium lentum* | + | | |
| *Flavobacterium meningiosepticum* | + | + | + |
| *Fusobacterium* | + | + | + |
| *Fusobacterium miningio* | + | + | + |
| *Haemophilia parainfluenza* | + | + | |
| *Haemophilis influenza* | + | + | + |
| *Haemophilus aphrophilus* | + | nd | nd |
| *Klebsiella oxytoca* | + | nd | nd |
| *Klebsiella pneumonia* | + | + | + |
| *Klebsiella rhinoscleromatis* | + | nd | nd |
| *Legionella micdliea* | + | | |
| *Legionella pneumophilia* | + | + | |
| *Leuconostoc lactic* | + | + | + |
| *Leuconostoc mesanteriodas* | + | + | + |
| *Listeria murrayi* | + | nd | nd |
| *Mima* | + | + | + |
| *Mycobacterium avium intracellulari* | + | | |
| *Mycobacterium flavescens* | + | + | |
| *Mycobacterium gordoniae* | + | | |
| *Mycobacterium terra* group | + | + | |
| *Mycobacterium tuberculoses* | + | | |
| *Neisseria cinerea* | + | nd | nd |
| *Neisseria gonorrhea* | + | | |
| *Neisseria lactamica* | + | | |
| *Neisseria meningiditis* | + | + | + |
| *Neisseria sicca* | + | | |
| *Nocardia brasiliensis* | + | nd | nd |
| *Pasteurella multocida* | + | nd | nd |
| *Proteus mirabilis* | + | + | + |
| *Proteus vulgaris* | + | + | + |
| *Pseudomonas cepatia* (strain I) | + | | + |
| *Pseudomonas cepatia* (strain II) | + | + | + |
| *Salmonella cholerasuis* | + | + | + |
| *Salmonella dublin* | + | + | + |
| *Salmonella muenchen* | + | + | + |
| *Salmonella paratyphi* | + | + | + |
| *Salmonella typhimurium* | + | + | + |
| *Serratia oderifera* | + | + | + |
| *Shigella boydii* | + | + | + |
| *Shigella dysenteriae* | + | + | + |
| *Shigella felxneri* | + | + | + |
| *Shigella sonneri* | + | + | + |
| *Staphylococcus aureus* | + | + | + |
| *Staphylococcus epi.* | + | + | + |
| *Staphylococcus saphrophy.* | + | + | + |
| *Streptococcus* alpha | + | + | |
| *Streptococcus* beta (Group C) | + | nd | nd |
| *Streptococcus* beta (Group F) | + | nd | nd |
| *Streptococcus bovis* | + | | + |
| *Streptococcus fecalis* | + | + | + |
| *Streptococcus* Group B | + | + | + |
| *Streptococcus mitis* | + | nd | nd |
| *Streptococcus mutans* | + | + | |
| *Streptococcus pneumonia* | + | + | |
| *Torulopsis globrata* | + | | |
| *Treponema denticola* | + | nd | nd |
| *Treponema pallidum* | + | nd | nd |
| *Treponema pertenue* | + | nd | nd |
| *Treponema phagedenis* | + | nd | nd |
| *Treponema refrigens* | + | nd | nd |
| *Vibro paruhen* | + | + | + |
| *Yersinia enterolitica* | + | + | + |

TABLE 4

Feasibility: Purified Organisms Tested Using PCR and Sequencing

| | Amplified Primer pairs: | | | Sequenced |
|---|---|---|---|---|
| Species | A* | B | C | A |
| *Alpha streptococcus* | + | + | | + |
| *Staphlococcus epi.* | + | + | + | + |
| *Streptococcus fecalis* | + | + | + | + |
| *Staphlococcus aureus* | + | + | + | + |
| *E. Coli* (unknown type) | + | + | + | + |
| *Pseudomonas cepatia* (I) | + | | + | + |
| *Acinetobacter* | + | + | + | + |
| *Haemophilus influenza* | + | + | + | + |
| *Enterobacter fecalis* | + | | | + |
| *Shigella sonneri* | + | + | + | + |
| *Serratia oderifera* | + | | + | + |
| *Klebsiella pneumonia* | + | + | + | + |
| *Proteus mirabilis* | + | + | + | + |
| *Chlamydia trachomatis* | + | | | + |
| *Staphlococcus saphrophy.* | + | + | + | + |
| *Candida albicans* | + | | | + |
| *Torulopsis globrata* | + | | | + |
| *Proteus vulgaris* | + | + | + | + |
| *Pseudomonas cepatia* (II) | + | + | + | + |
| *Shigella dysenteriae* | + | + | + | + |
| *Shigella felxneri* | + | + | + | + |
| *Shigella boydii* | + | + | + | + |
| *Salmonella muenchen* | + | + | + | + |
| *Salmonella typhimurium* | + | + | + | + |
| *Salmonella cholerasuis* | + | + | + | nd |
| *Salmonella dublin* | + | + | + | nd |
| *Salmonella paratyphi* | + | + | + | nd |
| *Aeromonas hydophila* | + | | | + |
| *Alteromonas putrifuciens* | + | + | + | + |
| *Mima* | + | + | | + |
| *Alcaligenes fecalis* | + | | | + |
| *Enterobacter cloecae* | + | + | + | + |
| *Enterobacter aerogenes* | + | + | + | + |
| *Fusobacterium miningio* | + | + | + | + |
| *Citrobacter fruendii* | + | + | + | + |
| *Vibro paruhen* | + | + | + | + |
| *Yersinia enterolitica* | + | + | + | + |
| *Leuconostoc lactic* | + | + | + | + |
| *Leuconostoc mesanteriodas* | + | + | + | + |
| *Actinobacillus* | + | + | + | + |
| *Actinomyces pyogenes* | + | + | + | + |
| *Bacteriodes fragila* | + | | | + |
| *Bacteriodes distasonis* | + | | | + |

TABLE 4-continued

Feasibility: Purified Organisms Tested Using PCR and Sequencing

| Species | Amplified Primer pairs: A* | B | C | Sequenced Primer pairs: A |
|---|---|---|---|---|
| *Bacteriodes melaninogenicus* | + | + | + | + |
| *Bacteriodes ovatus* | + | + | + | + |
| *Bacteriodes thetaiomicion* | + | + | + | + |
| *Bacteriodes uniformis* | + | + | + | + |
| *Clostridium difficile* | + | + | + | + |
| *Clostridium histolyticum* | + | + | + | + |
| *Clostridium perfingens* | + | + | + | + |
| *Clostridium sordelli* | + | + | + | + |
| *Clostridium septicum* | + | + | + | + |
| *Clostridium sporogenes* | + | + | + | + |
| *Eubacterium lentum* | + | | | + |
| *Fusobacterium* | + | + | + | + |
| *Actinomyces pyogenes* | + | + | + | + |
| *Corynebacterium pseudodoi.* | + | | | + |
| *Mycobacterium avium intracellulari* | + | | | + |
| *Streptococcus pneumonia* | + | + | | + |
| *Streptococcus* Group B | + | + | + | + |
| *Mycobacterium tuberculosis* | + | | | + |
| *Neisseria lactamica* | + | | | + |
| *Streptococcus mutans* | + | + | | + |
| *Aeromonas hydophilia* | + | + | | + |
| *Neisseria meningiditis* | + | + | + | + |
| *Alteromonas putriaciens* | + | + | + | + |
| *Legionella micdliea* | + | | | + |
| *Haemophilia parainfluenza* | + | + | | + |
| *Legionella pneumophilia* | + | + | | + |
| *Corynebacterium diptheria* | + | | | + |
| *Campylobacter* | + | + | | + |
| *Neisseria gonorrhea* | + | | | + |
| *Streptococcus bovis* | + | | + | + |
| *Mycobacterium gordoniae* | + | | | + |
| *Neisseria sicca* | + | | | + |
| *Mycobacterium terra* | + | + | | + |
| *Mycobacterium flavescens* | + | + | | + |
| *Aligella urethralis* | + | + | + | + |
| *Flavobacterium meningiosepticum* | + | + | + | + |
| *Treponema pallidum* | + | nd | nd | nd |
| *Treponema pertenue* | + | nd | nd | nd |
| *Treponema phagedenis* | + | nd | nd | nd |
| *Treponema denticola* | + | nd | nd | nd |
| *Treponema refrigens* | + | nd | nd | nd |
| Beta *streptococcus* (C) | + | nd | nd | nd |
| Beta *streptococcus* (F) | + | nd | nd | nd |
| *Listeria murrayi* | + | nd | nd | nd |
| *Nocardia brasiliensis* | + | nd | nd | nd |
| *Streptococcus mitis* | + | nd | nd | nd |
| *Haemophilus aphrophilus* | + | nd | nd | nd |
| *E. coli*-β lactamase+ | + | nd | nd | nd |
| *E. coli* 0157-H7 | + | nd | nd | nd |
| *Klebsiella rhinoscleroma.* | + | nd | nd | nd |
| *Klebsiella oxytoca* | + | nd | nd | nd |
| *Capnocytophaga* | + | nd | nd | nd |
| *Pasteurella multocida* | + | nd | nd | nd |
| CDC group IVc | + | nd | nd | nd |
| *Neisseria cinerea* | + | nd | nd | nd |

*Degenerate primers were synthesized from coordinates in the 16S rDNA sequence logo. Sequence confirmation was obtained with primer pair A.

EXAMPLE 11

Retrospective Clinical Study

Clinical samples containing microorganisms that have been identified were processed and analyzed according to the procedure disclosed in Examples 1-9. The main results obtained using the presently disclosed methods and those obtained using conventional microbiological methods are compared as shown in Table 5.

TABLE 5

Results of Retrospective Clinical Study

| Patient Hospital No. | Phylo Reference No. | Sample Type | Hospital Identification | (Amp. #) Primers | Experimenter | Phylogenetix ID Based on Blast Analysis | % Sequence Identity | Date Specimen Received |
|---|---|---|---|---|---|---|---|---|
| H53910 | 13I | MS Irrigation fluid | *S. aureus* - mod. | (2)A<br>(4)B*-reamp | M<br>D | *Staph. aureus* | 98 | Jun. 13, 1997 |
| T48753 | 14I | R. leg aspirate | *E. coli* - heavy<br>*Enterococcus* sp. - rare | (1)A<br>(2)B<br>(3)931* | M<br>N<br>N | *E. coli*<br>*E. coli* | 100<br>100 | Jun. 13, 1997 |
| T45000 | 16I | Peritoneal fluid | *S. marcescens* - mod. | (1)A<br>(2)B<br>(3)A<br>(3)931-A* | M<br>N<br>N<br>N | *Legionella*<br>*S. marcescens* and others<br>*Ser. marcescens* | 92<br>98<br>97 | Jun. 13, 1997 |
| T46015 | 17I | Abdominal fluid | *E. coli* - rare | (1)A<br>(2)B<br>(3)931* | M<br>N<br>N | *E. coli*<br>*E. coli* | 100<br>99 | Jun. 13, 1997 |
| W48038 | 20I | CSF | *S. marcescens* - rare | (2)A | M | *Serratia marcescens* | 99 | Jun. 13, 1997 |
| X25530 | 22I | Peritoneal fluid | *S. aureus* | (1)A*<br>(2)B<br>(3)A<br>(3)931-A* | M<br>N<br>N<br>N | *Staph. aureus*<br>*Staph. aureus* | 100<br>100<br>99 | Jun. 13, 1997 |
| X25803 | 24I | Ventricular CSF | *S. aureus* - mod. | (1)A<br>(2)B<br>(3)931* | M<br>N<br>N | *S. aureus*<br>*Staph. aureus* | 100<br>99 | Jun. 13, 1997 |

TABLE 5-continued

Results of Retrospective Clinical Study

| Patient Hospital No. | Phylo Reference No. | Sample Type | Hospital Identification | (Amp. #) Primers | Experimenter | Phylogenetix ID Based on Blast Analysis | % Sequence Identity | Date Specimen Received |
|---|---|---|---|---|---|---|---|---|
| F46714 | 25I | Peritoneal fluid | *S. marcescens* - rare | (1)A | M | *Legionella* | 93 | Jun. 13, 1997 |
| | | | | (2)B | N | *S. marcescens* | 97 | |
| | | | | (2)931* | N | | | |
| | | | | (3)A | N | *Ser. marcescens* | 97 | |
| | | | | (3)931-A* | N | | | |
| W48390 | 26I | Knee fluid | Grp. B *Strep.* - mod. | (3)A* | M | | | Jun. 13, 1997 |
| | | | | (4)B | N | *Strep.* | 100 | |
| | | | | (5)A* | N | | | |
| | | | | (5)931-A* | N | | | |
| X25714 | 27I | Jackson pratt fluid | *Enterobacter cloacae* - heavy | (1)A | M | *Enterobacter Klebsiella* | 99 | Jun. 13, 1997 |
| | | | | (2)B | N | *Enterobact.* sp., *Kleb.* sp. | 98 | |
| | | | | (3)931* | N | | | |
| H53080 | 28I | CSF | *S. marcescens* - light | (1)A | M | *S. marcescens* | 90 | Jun. 13, 1997 |
| | | | | (2)B* | N | | | |
| | | | | (3)A* | N | | | |
| | | | | (3)931-A* | N | | | |
| T48303 | 29I | RLQ drain | *Enterococcus* sp. - mod. CNS - mod. *Candida albicans* (fungus)- mod. | (1)A* | M | | | Jun. 13, 1997 |
| | | | | (2)B | N | *Lactobacillus* sp., *Enterocooccus* sp. | 100 100 | |
| | | | | (3)A | N | *Enterococcus* | 100 | |
| M69761 | 34I | T/tube fluid | *Enterobacter sakaqaii* *Enterococcus* sp | (1)A | M | *Enterobacter sakagaii Klebsiella* | 99 BF-100 | Aug. 19, 1997 |
| | | | | (2)B | N | *E. coli*, *Kleb.* sp., *Enterobac.* sp. | 100 | |
| | | | | (3)931 | N | *Enterobacter sakagaii* | 97 97 | |
| T827 | 36I | Pancreatic fluid | CNS *Strep. viridans* | (1)A | M | *Streptococcus viridans* | 89 | Aug. 19, 1997 |
| | | | | (2)B* | N | | | |
| | | | | (3)B* | N | | | |
| | | | | (4)A | N | *Strep. viridans* | 88 | |
| W9648 | 39I | CSF | MRSA - heavy | (1)A | M | *Staphylococcus* | 100 | Sep. 9, 1997 |
| | | | | (3)B | N | *Legionella* | 92 | |
| X42186 | 41I | T-tube | *Candida albicans* (fungus)- heavy CNS Meth. resistant - heavy *Eikenalla carrodens* - mod. *Candida tropicalis* (fungus)- heavy | (1)A | M | *Staphylococcus* | 99 | Sep. 9, 1997 |
| | | | | (2)B* | N | | | |
| | | | | (2)931* | N | | | |
| | | | | (3)B | N | *Staph* | 100 | |
| T9271 | 50I | CSF | *Staph. aureus* - light | (1)A | M | *Staph. aureus* | 100 | Sep. 9, 1997 |
| | | | | (2)B | N | *Staph. aureus* | 100 | |
| | | | | (2)931* | N | | | |
| F12076 | 54I | Bile | *Enterobacter cloacae* - heavy *Enterococcus* sp. - light *Klebsiella oxytoca* - light *Candida albicans* (fungus)- light | (1)A | M | *Klebsiella oxytoca* *Enterobacter cloacae* | 100 100 100 100 | Sep. 30, 1997 |
| | | | | (2)B | N | *Kleb. oxytoca* | 100 | |
| X46327 | 55I | Bile | *Klebsiella oxytoca* - heavy *E. coli* - heavy *Enterococcus* sp - heavy *Strep. viridans* - heavy | (1)A | M | *Klebsiella Oxytoca* | 100 | Sep. 30, 1997 |
| | | | | (2)B | N | *Kleb. oxytoca* *Enterobacteria* sp. | 99 99 | |
| H33952 | 58I | Aqueous humor (eye) | *Strep. pneumo.* - heavy | (1)A* | M | | | Oct. 20, 1997 |
| | | | | (2)B | N | *Strep. pneumoniae* | 100 | |
| | | | | (2)931* | N | | | |
| | | | | (3)A | D | *Strep. pneumoniae* | 95 | |
| M26174 | 60I | Left pleural fluid | *Enterococcus* sp. - rare | (2)A | M | *Enterococcus* | 100 | Nov. 18, 1997 |
| | | | | (3)B | N | *Enterococcus* | 100 | |
| M26178 | 61I | Right pleural fluid | *Enterococcus L sp.* - rare | (2)A | M | *Enterococcus* | 100 | Nov. 18, 1997 |
| | | | | (3)B | N | *Enterococcus* | 100 | |
| X52908 | 64I | Abscess fluid | *Enterobacter aerogenes* - heavy | (1)A | M | *Enterobacter aerogenes* | 100 | Nov. 18, 1997 |
| | | | | (2)B | N | *Enterobacter aerogenes* | 98 | |
| H34581 | 66I | Pelvic abscess | *Peptostrep* sp. - mod. *Bacteriodes caccae* - mod. | (2)A | M | *Peptostreptococcus* | 96 | Nov. 18, 1997 |
| | | | | (3)B | N | *Strep.* sp. | 100 | |
| H36540 | 67I | Liver fluid | *Bacteriodes coccae* *Bacteriodes fragelis* *Prop. granulosum* | (1)A | M | *B. fragilis* | 93 | Nov. 18, 1997 |
| | | | | (2)B | N | *Lactobacillus* (several) | 100 | |
| F26285 | 68I | Fluid | *Bacteriodes coccae* *Bacteriodes thetarotaomcron* | (1)A | M | *Bacteriodes* | 98 | Nov. 18, 1997 |
| | | | | (2)B | N | *Bacteriodes* | 99 | |

TABLE 5-continued

Results of Retrospective Clinical Study

| Patient Hospital No. | Phylo Reference No. | Sample Type | Hospital Identification | (Amp. #) Primers | Experimenter | Phylogenetix ID Based on Blast Analysis | % Sequence Identity | Date Specimen Received |
|---|---|---|---|---|---|---|---|---|
| | | | *Bacteriodes melanogencus* *Bacteriodes loeschiu/dentiediu* | | | | | |
| H41847 | 70I | Thoracentesis | *Strep. bovis* | (1)A | M | *Streptococcus bovis* | 97 | Nov. 18, 1997 |
| | | | | (2)B | N | *Strep. bovis* | 100 | |
| T35608 | 72I | Pleural fluid | *Ps. aeruginosa* *Enterococcus* sp. *Candida parapsilosis* (fungus) | (2)A | M | *Pseudomonas aeruginosa* | 98 | Nov. 18, 1997 |
| | | | | (3)B | N | *Ps. aeruginosa* | 98 | |
| S67044 | 74I | CSF | *Acinetobacter calcoacetieus* | (1)A | M | *Acinetobacter calcoacetieus* | 99 100 | Nov. 18, 1997 |
| | | | | (2)B | N | *Acinetobacter calcoacetieus* | 99 | |
| F32952 | 76I | Fluid from heel | *Ser. marcescens* *Enterococcus* | (1)A | M | *Serratia marcescens* | 100 | Dec. 16, 1997 |
| | | | | (3)B | N | *Ser. marcescens* | 97 | |
| M38413 | 77I | Abscess - kidney | *E. coli* | (2)A | M | *E. coli* | 100 100 | Dec. 16, 1997 |
| | | | | (3)B | N | *E. coli* | 97 | |
| T38404 | 78I | Nephrostomy fluid | *Ser. marcescens* | (2)A | M | *S. marcescens* | 98 | Dec. 16, 1997 |
| | | | | (3)B | N | *Ser. marcescens* | 97 | |
| T43701 | 86I | Bile | *Serratia liquifaciens* | (1)A* | M | | | Dec. 16, 1997 |
| | | | | (2)B | N | *Serratia liguifaciens* | 98 | |
| | | | | (2)931* | N | | | |
| | | | | (3)A | N | *Ser. liguifaciens* | 99 | |
| | | | | (3)931-A | N | *Ser. liguifaciens* | 92 | |
| S919 | 87I | Peritoneal fluid | Coag. neg. *staph* | (1)A | M | *Staphylococcus* | 97 | Dec. 16, 1997 |
| | | | | (2)B | N | *Staph.* ( | 100 | |
| X62355 | 88I | Elbow fluid | B Group A strep | (1)A | M | *Streptococcus* | 100 | Dec. 16, 1997 |
| | | | | 2(B) | N | *Strep.* | 100 | |
| M46066 | 89I | Asperata | *Entero* sp. *Coryne* sp. | (1)A* | M | | | Dec. 16, 1997 |
| | | | | (2)B | N | *Enterococcus* sp. | 98 | |
| | | | | (2)931* | N | | | |
| | | | | (3)A* | N | | | |
| | | | | (3)931-A* | N | | | |
| M46395 | 90I | Pleural fluid | *Kleb. pneumonae* *Coryne* sp. | (1)A | M | *K. pneumoniae* | 96 | Dec. 16, 1997 |
| | | | | (2)B | N | *Kleb. pneumoniae* | 98 | |
| M47004 | 91I | Synovial fluid | Beta *strep* A | (2)A | M | *Streptococcus* | 100 | Dec. 16, 1997 |
| | | | | (3)B | N | *Strep.* | 93 | |
| M47005 | 92I | Elbow fluid | Beta *strep* A | (1)A* | M | | | Dec. 16, 1997 |
| | | | | (2)B | N | *Strep.* | 100 | |
| | | | | (2)931* | N | | | |
| | | | | (3)A | N | *Strep.* | 98 | |
| | | | | (3)931-A* | N | | | |
| F42928 | 94I | Abdominal fluid | *S. aureus* | (2)A | M | *S. aureus* | 100 | Dec. 16, 1997 |
| | | | | (3)B | N | *Staph. aureus* | 100 | |
| F43164 | 95I | Bile | *Ps. aeruginosa* *Enterococcus* sp. | (1)A* | M | | | Dec. 16, 1997 |
| | | | | (2)B | N | *Pseudomonas aeruginosa* | 96 | |
| | | | | (3)931 | N | | 97 | |
| | | | | (4)A | N | *Pseudomonas aeruginosa* | 98 | |
| | | | | (4)931-A* | N | *Pseudomonas. aeruginosa* | | |
| F45280 | 96I | JP drainage | *Strep ocudans* *Coryne* sp. Coag. Neg. *Staph.* | (2)A | M | *Streptococcus ocudans* | 98 | Jan. 6, 1998 |
| | | | | (3)B* | N | | | |
| | | | | (4)B | N | *Strep. ocudans* | 100 | |
| T50295 | 100I | CSF | Coag. Heg. *Staph.* | (1)A | M | *Staphylococcus* | 100 | Jan. 6, 1998 |
| | | | | (2)B | N | *Staph.* | 100 | |
| W60881 | 107I | Bile | *K. pneumo* *Enterococcus* *Lactobacillus* Yeast | (1)A | M | *Lactobacillus* | 98 | Jan. 15, 1998 |
| | | | | (2)B | N | *Lactobacillus* sp. | 100 | |
| | | | | (3)931 | N | *Lactobacillus* | 97 | |
| T55158 | 109I | Chest drainage | *Ent. faecium* | (1)A* | M | | | Jan. 15, 1998 |
| | | | | (2)B | N | *Ent. faecium* | 100 100 | |
| | | | | (3)A* | N | | | |
| | | | | (3)931-A* | N | | | |
| | | | | (4)A* | N | | | |
| X68623 | 112I | ICP fluid | Coag. Neg. *Staph.* | (1)A | M | *Legionella* | 90 | Feb. 19, 1998 |
| | | | | (4)A | D | *Staph* | 98 | |
| | | | | (4)B* | D | | | |

TABLE 5-continued

Results of Retrospective Clinical Study

| Patient Hospital No. | Phylo Reference No. | Sample Type | Hospital Identification | (Amp. #) Primers | Experi- menter | Phylogenetix ID Based on Blast Analysis | % Sequence Identity | Date Specimen Received |
|---|---|---|---|---|---|---|---|---|
| S12277 | 113I | Pelvic fluid | E. coli | (1)A | M | E. coli | 100 | Feb. 19, 1998 |
|  |  |  | Enterococcus sp. | (2)B | N | E. coli | 100 |  |
|  |  |  | C. albicans (fungus) |  |  |  |  |  |
|  |  |  | Coag. Neg. Staph. |  |  |  |  |  |
| S12826 | 114I | Elbow fluid | S. aureus | (2)A | M | Staph. aureus | 100 | Feb. 19, 1998 |
|  |  |  |  | (3)B | N | Staph. aureus | 95 |  |
| X529 | 115I | CSF | Coag. Neg. Staph. | (1)A | M | Streptococcus xylosus | 95 | Feb. 19, 1998 |
|  |  |  |  | (2)B | N | Staph. | 100 |  |
| X530 | 116I | CSF | Coag. Neg. Staph. | (1)A | M | Staph. | 100 | Feb. 19, 1998 |
|  |  |  |  | (2)B | N | Staph. | 100 |  |
| F1545 | 117I | Joint (bursa) fluid | S. aureus | (1)A | M | Staph. aureus | 100 | Mar. 4, 1998 |
|  |  |  |  | (2)B | N | Staph. aureus | 100 |  |
| M7133 | 122I | Bile | C. albicans (fungus) | (1)A | M | Streptococcus viridans | 96 | Mar. 4, 1998 |
|  |  |  | Strep. viridans |  |  | Streptococcus viridans |  |  |
| M26418 | 126I | Abdominal fluid | Ps aeruginosa | (3)A | M | Ps. aeruginosa | 100 | May 7, 1998 |
|  |  |  |  |  |  | Ps. aeruginosa |  |  |
|  |  |  |  | (4)B | N | Ps. aerug. | 98 |  |
| F26979 | 127I | Bile | Ps aeruginosa | (1)A* | M |  |  | May 7, 1998 |
|  |  |  | C. albicans (fungus) | (2)A* | M |  |  |  |
|  |  |  | Enterococcus sp | (3)A | M | Ps. aeruginosa | 100 |  |
|  |  |  |  | (4)B | N | Ps. aeruginosa | 96 |  |
|  |  |  |  | (5)931 | M | Ps. aeruginosa | 99 |  |
| F26350 | 128I | Pelvic abscess | C. albicans (fungus) | (3)A* | M |  |  | May 7, 1998 |
|  |  |  | CNS | (4)B | N | Bacteriodes | 97 |  |
|  |  |  | E. coli |  |  | thetaiotaomicron |  |  |
|  |  |  | B. vulgalis |  |  |  |  |  |
|  |  |  | B. thetaiotaomicron |  |  |  |  |  |
| F28102 | 131I | CSF | Ent. cloacae | (1)A | M | Enterobacter cloacae | 99 | May 7, 1998 |
|  |  |  |  | (3)B | N | Ent. cloacae | 98 |  |
| S18864 | 132I | CSF | Ent. cloacae | (1)A | M | Enterobacter cloacae | 99 | May 7, 1998 |
|  |  |  |  | (2)B | N | Ent. cloacae | 97 |  |
|  |  |  |  | (3)931 | N | Ent. cloacae | 99 |  |
|  |  |  |  |  |  |  | 99 |  |
| X16529 | 137I | CSF | Ent. cloacae | (1)A | M | Enterobacter cloacae | 100 | Jun. 10, 1998 |
|  |  |  |  | (2)B | N | Enterobac. cloacae | 100 |  |
|  |  |  |  | (3)931 | N | Enterobacter cloacae | 99 |  |
| F32412 | 139I | CSF | Ent. cloacae | (1)A | M | Enterobacter sp. | 100 | Jun. 10, 1998 |
|  |  |  | Ent. freundii |  |  |  | 100 |  |
|  |  |  |  | (2)B | N | Enterbac. sp. | 98 |  |
|  |  |  |  | (2)931* | N |  |  |  |
| W39152 | 147I | Fluid around liver | Ps. aeruginosa | (1)A | M | Ps. aeruginosa | 99 | Jun. 10, 1998 |
|  |  |  | Coag. Heg. Staph. | (2)B | N | Ps. aeruginosa | 100 |  |
|  |  |  |  | (3)931* | N |  |  |  |
| M38970 | 148I | Abdominal fluid | K. pneumo | A | N | Prevotella bivia | 98 | Jun. 10, 1998 |
|  |  |  | Prevotella bivia | B | N | Prevotella bivia | 94 |  |
|  |  |  |  | 931 | N | Prevotella bivia | 97 |  |
|  |  |  |  | 1462* | N |  |  |  |
| M55048 | 149I | ICP fluid | Coag. Neg. Staph | A | N | Staph. | 100 | Jul. 23, 1998 |
|  |  |  |  |  |  |  | 100 |  |
|  |  |  |  | B | N | Staph. | 95 |  |
|  |  |  |  | 931* | N |  |  |  |
|  |  |  |  | 1462* | N |  |  |  |
| F29060 | 152I | Bile | Ent. freundii | (1)A | N | Staph | 100 | Jul. 23, 1998 |
|  |  |  | Enterococcus sp. | (1)B* | N |  |  |  |
|  |  |  | Strep. viridans | (1)931* | N |  |  |  |
|  |  |  | C. albicans (fungus) | (2)B | N | Ent. sp. | 98 |  |
|  |  |  | C. glabrata (fungus) |  |  |  |  |  |
| T43605 | 169I | Aspirate | Strep. viridans | (2)A* | N |  |  | Jan 17, 1998 |
|  |  |  |  | (4)A | N | Strep. viridans | 99 |  |
|  |  |  |  | (5)B* | N |  |  |  |
|  |  |  |  | (6)B* | D |  |  |  |
| F54210 | 173I | Chest tube drainage | Enterococcus sp. - light | (4)B* | N | Enterococcus sp | 94 | Mar. 15, 1999 |
| F53870 | 174I | Pleural fluid | Ent. aerogenes - mod. | (4)B | N | Ent. aerogenes |  | Mar. 15, 1999 |
| W14514 | 183I | pleural fluid | Strep. pneumoniae- mod | (3)A | D | Strep. pneumoniae | 99 | Apr. 19, 1999 |
|  |  |  |  | (3)B | D | Strep. pneumoniae | 94 ## |  |

The results in Table 5 show that in vast majority of the cases, identification using the methods and the primer sets disclosed here produce the same results as those identified using conventional culturing methods. Of the 299 total clinical samples tested, 195 samples produced either positive or negative amplification results that are in accord with the results obtained by culturing method. Of the 145 positive amplification products sequenced, 131 produced acceptable sequence results. 114 of the 131 sequence results identified the same organism(s) as the culturing method, with one result generating more specific identification of the organism than the traditional culturing method. 4 out of 131 produced identification results that are in discordance with the results produced by culturing. An additional 12 sequencing results appeared to contain multiple sequences likely as a result of multiple organisms in the clinical sample.

What is claimed is:

1. A method for obtaining data for taxonomic assignment of unknown species comprising:

(a) selecting from more than one known species a divergent segment of DNA with low average information content surrounded by two conserved segments of DNA wherein said conserved segments comprise DNA segments with high average information content and wherein information content is determined by average information in bits of a related set of sequences and represents the total sequence conservation calculated by:

$$R_{sequence} = 2 - [-\Sigma f(b,l)\log 2f(b,l)+e(n(l))]b=[A,G,C,T]$$

wherein f(b,l) is the frequency of each base b (A,G,C, and T) at position l, and e(n(l)) is a generalized correction term determined by Shannon's Uncertainty for a sample size n at position l, (b) selecting primers for PCR amplification of said divergent segment such that said primers anneal to said conserved segments in any of these one or more unknown species, wherein each primer contains a mixture of nucleotides in which each nucleotide is present at the same proportion as it is present in the set of sequences of the known species used to compute the information content;

(c) amplifying said divergent segment of DNA by PCR technique using said primers to obtain PCR products;

(d) separating said PCR products;
(e) comparing said separated PCR products with a database consisting of properties that can be converted or derived from a subject sequence and from similar sequences distinguishable from the subject sequence, wherein said properties are selected from the group consisting of nucleotide composition, base composition, nucleotide sequence, DNA structure, mass ratio of the DNA molecules or fragments derived therefrom, chemical reactivity of the DNA molecules, binding properties to other DNA molecules or proteins, thermal stability, and combination thereof;
(f) measuring a taxonomic distance of said properties between said separated PCR products and organisms in said database; and
(g) assigning a taxonomic reference to said separated PCR products based upon said properties.

2. The method of claim 1, wherein the selecting said divergent segment of DNA surrounded by said conserved segments is performed in the region of the DNA coding for the ribosomal RNA of any organism.

3. The method of claim 2, wherein said ribosomal RNA is the 28S ribosomal RNA from eukaryotic organisms or the 16S ribosomal RNA from prokaryotic organisms.

4. The method of claim 3, wherein the separated PCR products are characterized based upon nucleotide sequence.

5. The method of claim 4, wherein sequences of the separated PCR products are determined by mass spectrometry.

6. The method of claim 3, wherein the PCR products are separated by means selected from the group consisting of magnetic separation, gel purification, mass spectrometry, and combination thereof.

7. The method of claim 6, wherein the PCR products are separated by gel purification.

8. The method of claim 6, wherein the PCR products are separated by denaturing gel electrophoresis.

9. The method of claim 3, wherein steps (d) and (e) are accomplished by mass spectrometry.

10. A method for identifying an organism in a sample, comprising:
(a) selecting from more than one known species a divergent segment of DNA with low average information content surrounded by two conserved segments of DNA wherein said conserved segments comprise DNA segments with high average information content and wherein information content is determined by average information in bits of a related set of sequences and represents the total sequence conservation calculated by:

$$R_{sequence}=2-[-\Sigma f(b,l)\log 2f(b,l)+e(n(l))]b==[A,G,C,T]$$

wherein
f(b,l) is the frequency of each base b (A,G,C, and T) at position l, and
e(n(l)) is a generalized correction term determined by Shannon's Uncertainty for a small sample size n at position l,
(b) selecting primers for PCR amplification of said divergent segment such that said primers anneal to said conserved segments in any of these one or more unknown species, wherein each primer contains a mixture of nucleotides in which each nucleotide is present at the same proportion as it is present in the set of sequences of the known species used to compute the information content;
(c) amplifying said divergent segment of DNA by PCR technique using said primers to obtain PCR products;
(d) separating said PCR products;
(e) comparing said separated PCR products with a database consisting of properties that can be converted or derived from a subject sequence and from similar sequences distinguishable from the subject sequence, wherein said properties are selected from the group consisting of nucleotide composition, base composition, nucleotide sequence, DNA structure, mass ratio of the DNA molecules or fragments derived therefrom, chemical reactivity of the DNA molecules, binding properties to other DNA molecules or proteins, thermal stability, and combination thereof; and
(f) identifying one or more organisms in said separated PCR products based upon properties.

11. The method of claim 10, further comprising a sample processing step to be performed before step (c), said sample processing step being selected from the group consisting of lysis of red blood cells, removal or addition of salts, sample concentration and sample dilution.

12. The method of claim 10, further comprising a step wherein the existence of a pathological condition or a disease in an individual is determined base upon the identity of said organism obtained in steps (a)-(f).

13. The method of claim 10, wherein the selecting said divergent segment of DNA surrounded by said conserved segments is performed in the region of the DNA coding for the ribosomal RNA of any organism.

14. The method of claim 13, wherein said ribosomal RNA is the 28S ribosomal RNA from eukaryotic organisms or the 16S ribosomal RNA from prokaryotic organisms.

15. The method of claim 14, wherein the separated PCR products are characterized identified based upon nucleotide sequence.

16. The method of claim 15, wherein sequences of the separated PCR products are determined by mass spectrometry.

17. The method of claim 16, wherein the PCR products are separated by means selected from the group consisting of magnetic separation, gel purification, mass spectrometry, and combination thereof.

18. The method of claim 17, wherein the PCR products are separated by gel purification.

19. The method of claim 17, wherein the PCR products are separated by denaturing gel electrophoresis.

20. The method of claim 14, wherein steps (d), (e) and (f) are accomplished by mass spectrometry.

21. The method of claim 12, wherein said organism is from at least one species selected from the group consisting of *Acinetobacter, Actinobacillus, Actinomyces pyogenes, Actinomyces pyogenes, Aeromonas hydrophila, Alcaligenes fecalis, Aligella urethralis, Alteromonas putriaciens, Alteromonas putrifuciens, Bacteriodes distasonis, Bacteriodes fragila, Bacteriodes melaminogenicus, Bacteriodes ovatus, Bacteriodes thetaiomicion, Bacteriodes uniformis, Campylobacter, Candida albicans, Capnocytophaga,* CDC group Ivc, *Chlamydia trachomatis, Citrobacter fruendii, Clostridium difficle, Clostridium histolyticum, Clostridium perfingens, Clostridium septicum, Clostridium sordelli, Clostridium sporogenes, Corynebacterium diptheria, Corynebacterium pseudodoi, E. coli, E. coli* 0157-H7, *E. coli*-beta lactamase positive, *Enterobacter aerogenes, Enterobacter cloecae, Enterobacter fecalis, Eubacterium lentum, Flavobacterium meningiosepticum, Fusobacterium, Fusobacterium miningio, Haemophilia parainfluenza, Haemophilis influenza, Haemophilus aphrophilus, Klebsiella oxytoca, Klebsiella pneumonia, Klebsiella rhinosclaromatis, Legionella micdliea, Legionella pneumophilia, Leuconostoc lactic, Leu-* conostoc mesanteriodas, Listeria murrayi, Mima, Mycobacterium avium intracellulari, Mycobacterium flavescens, Mycobacterium gordoniae, Mycobacterium terra group, Mycobacterium tuberculoses, Neisseria cinerea, Neisseria gonorrhea, Neisseria lactamica, Neisseria meningitidis, Neisseria sicca, Nocardia brasiliensis, Pasteurella multocida, Proteus mirabilis, Proteus vulgaris, Pseudomonas cepatia (strain I), Pseudomonas cepatia (strain II), Salmonella cholerasuis, Salmonella dublin, Salmonella muenchen, Salmonella paratyphi, Salmonella typhimurium, Serratia oderifera, Shigella boydii, Shigella dysenteriae, Shigella felxneri, Shigella sonneri, Staphylococcus aureus, Staphylococcus epi., Staphylococcus saphrophy, Streptococcus alpha, Streptococcus beta (Group C), Streptococcus beta (Group F), Streptococcus bovis, Streptococcus fecalis, Streptococcus Group B, Streptococcus mitis, Streptococcus mutans, Streptococcus pneumonia, Torulopsis globrata, Treponema denticola, Treponema pallidum, Treponema pertenue, Treponema phagedenis, Treponema refrigens, Vibro paruhen, and Yersinia enterolitica.

22. The method of claim 10, wherein said primers for PCR amplification comprise Forward:
(SEQ ID. NO. 1)
5'- G T G$(C_{0.988}/G_{0.006}/T_{0.006})$ CAGC $(A_{0.95}/C_{0.038}/$ $G_{0.006}/T_{0.006})$ G $(C_{0.994}/T_{0.006})$ $(A_{0.006}/C_{0.982}/$ $G_{0.006}/T_{0.006})$ $(C_{0.006}/G_{0.988}/T_{0.006})$ $(C_{0.994}/$ $T_{0.006})$ G G T -3'

Reverse:
(SEQ ID. NO. 2)
5'- C C$(C_{0.994}/A_{0.006})$ $(T_{0.006}/G_{0.988}/A_{0.006})$ $(T_{0.939}/C_{0.055}/A_{0.006})$ C $(T_{0.041}/A_{0.959})$ A T $(T_{0.988}/$ $C_{0.006}/A_{0.006})$ $(T_{0.033}/C_{0.961}/A_{0.006})$ $(T_{0.006}/$ $G_{0.006}/C_{0.853}/A_{0.135})$ $(T_{0.994}/C_{0.006})$ T $(T_{0.994}/$ $G_{0.006})$ $(G_{0.922}/A_{0.072}/C_{0.006})$ $(A_{0.994}/G_{0.006})$ $(G_{0.994}/C_{0.006})$ T $(T_{0.994}/A_{0.006})$ $(T_{0.994}/G_{0.006})$ -3' wherein the subscripts represent the relative abundance of the corresponding nucleotide at that position in the sequence as determined by information analysis of sequences from prokaryotic species.

23. The method of claim 10, wherein said primers for PCR amplification comprise Forward:
(SEQ ID. NO. 3)
5'- $(G_{0.954}/T_{0.043}/A_{0.002}/C_{0.001})$ $(G_{0.978}/C_{0.02}/$ $T_{0.002})$ $(T_{0.9985}/G_{0.0015})$ $(T_{0.992}/C_{0.006}/A_{0.002})$ $(A_{0.989}/C_{0.004}/T_{0.007})$ $(A_{0.998}/T_{0.002})$ $(G_{0.998}/$ $A_{0.002})$ $(G_{0.003}/C_{0.001}/T_{0.996})$ $(C_{0.975}/G_{0.021}/$ $T_{0.004})$ $(C_{0.952}/A_{0.042}/T_{0.005}/C_{0.001})$ $(A_{0.009}/C_{0.882}/$ $G_{0.063}/T_{0.046})$ $(A_{0.052}/C_{0.002}/G_{0.943}/T_{0.003})$ $(A_{0.005}/C_{0.890}/G_{0.003}/T_{0.102})$ A A C G A -3'

Reverse:
(SEQ ID. NO.4)
5'- C A$(T_{0.996}/C_{0.002}/A_{0.002})$ $(T_{0.996}/G_{0.002}/$ $A_{0.002})$ G $(C_{0.005}/T_{0.995})$ A $(T_{0.062}/G_{0.914}/A_{0.024})$ $(T_{0.074}/G_{0.039}/C_{0.887})$ $(T_{0.004}/G_{0.008}/C_{0.043}/$ $A_{0.945})$ $(T_{0.097}/C_{0.903})$ G $(T_{0.911}/C_{0.088}/A_{0.001})$ $(G_{0.982}/T_{0.018})$ T $(G_{0.998}/C_{0.002})$ $(T_{0.834}/C_{0.036}/$ $A_{0.130})$ $(A_{0.032}/C_{0.029}/G_{0.057}/T_{0.882})$ C C C -3' wherein the subscripts represent the relative abundance of the corresponding nucleotide at that position in the sequence as determined by information analysis of sequences from prokaryotic species.

24. The method of claim 10, wherein said primers for PCR amplification comprise Forward:
(SEQ ID. NO. 5)
5'- $(G_{0.954}/T_{0.043}/A_{0.002}/C_{0.001})$ $(G_{0.978}/C_{0.02}/$ $T_{0.002})$ $(T_{0.9985}/G_{0.0015})$ $(T_{0.992}/C_{0.006}/A_{0.002})$ $(A_{0.989}/C_{0.004}/T_{0.007})$ $(A_{0.998}/T_{0.002})$ $(G_{0.998}/$ $A_{0.002})$ $(G_{0.003}/C_{0.001}/T_{0.996})$ $(C_{0.975}/G_{0.021}/$ $T_{0.004})$ $(C_{0.952}/A_{0.042}/T_{0.005}/G_{0.001})$ $(A_{0.009}/$ $C_{0.882}/G_{0.063}/T_{0.046})$ $(A_{0.052}/C_{0.002}/G_{0.943}/T_{0.003})$ $(A_{0.005}/C_{0.890}/G_{0.003}/T_{0.102})$ A A C G A - 3'

Reverse:
(SEQ ID. NO. 6)
5'- $(T_{0.996}/A_{0.002}/G_{0.002})$ $(C_{0.994}/G_{0.001}/T_{0.005})$ $(T_{0.993}/C_{0.005}/G_{0.002})$ $(G_{0.995}/C_{0.001}/A_{0.004})$ $(A_{0.996}/T_{0.0025}/C_{0.0015})$ $(C_{0.997}/A_{0.0015}/G_{0.0015})$ G $(G_{0.998}/A_{0.002})$ $(G_{0.996}/C_{0.004})$ $(C_{0.998}/G_{0.002})$ $(G_{0.971}/A_{0.027}/C_{0.002})$ G T $(G_{0.999}/T_{0.001})$ $(T_{0.953}/$ $A_{0.047})$ G T $(A_{0.946}/G_{0.054})$ C A -3' wherein the subscripts represent the relative abundance of the corresponding nucleotide at that position in the sequence as determined by information analysis of sequences from prokaryotic species.

* * * * *

UNITED STATES PATENT AND TRADEMARK OFFICE
CERTIFICATE OF CORRECTION

| | | |
|---|---|---|
| PATENT NO. | : 8,076,104 B2 | Page 1 of 1 |
| APPLICATION NO. | : 12/011425 | |
| DATED | : December 13, 2011 | |
| INVENTOR(S) | : Peter K. Rogan | |

It is certified that error appears in the above-identified patent and that said Letters Patent is hereby corrected as shown below:

On the Title Page, Item (76) Inventors address should be

1630 Phillbrook Drive
London, ON N5X2V8
Canada

Signed and Sealed this
Twelfth Day of June, 2012

David J. Kappos
*Director of the United States Patent and Trademark Office*